(12) United States Patent
Pérez et al.

(10) Patent No.: US 9,375,459 B2
(45) Date of Patent: Jun. 28, 2016

(54) CYCLIC PEPTIDES WITH AN ANTI-NEOPLASIC AND ANTI-ANGIOGENIC ACTIVITY

(75) Inventors: María del Carmen Abrahantes Pérez, Havana (CU); Glay Chinea Santiago, Havana (CU); Eduardo Martínez Diaz, Havana (CU); Hilda Elisa Garay Pérez, Havana (CU); Osvaldo Reyes Acosta, Havana (CU); Ernesto Lopez Mola, Havana (CU); Cruz Matilde Lopez Abad, Havana (CU); Sonia Gonzalez Blanco, Havana (CU)

(73) Assignee: CENTRO DE INGENIERIA GENETICA BIOTECNOLGIA, La Habana (CU)

( * ) Notice: Subject to any disclaimer, the term of this patent is extended or adjusted under 35 U.S.C. 154(b) by 111 days.

(21) Appl. No.: 14/005,855

(22) PCT Filed: Mar. 21, 2012

(86) PCT No.: PCT/CU2012/000002
§ 371 (c)(1),
(2), (4) Date: Dec. 31, 2013

(87) PCT Pub. No.: WO2012/126441
PCT Pub. Date: Sep. 27, 2012

(65) Prior Publication Data
US 2014/0112976 A1     Apr. 24, 2014

(30) Foreign Application Priority Data
Mar. 21, 2011   (CU) .................................. 2011/0067

(51) Int. Cl.
| | | |
|---|---|---|
| *A61K 38/12* | (2006.01) | |
| *A61K 31/4025* | (2006.01) | |
| *A61K 45/06* | (2006.01) | |
| *C07K 7/64* | (2006.01) | |
| *C07K 7/06* | (2006.01) | |
| *C07K 7/08* | (2006.01) | |
| *A61K 47/48* | (2006.01) | |
| *A61K 38/00* | (2006.01) | |
| *A61K 9/00* | (2006.01) | |
| *A61K 9/127* | (2006.01) | |
| *A61K 9/50* | (2006.01) | |

(52) U.S. Cl.
CPC ............ *A61K 38/12* (2013.01); *A61K 31/4025* (2013.01); *A61K 45/06* (2013.01); *A61K 47/48215* (2013.01); *C07K 7/06* (2013.01); *C07K 7/08* (2013.01); *C07K 7/64* (2013.01); *A61K 9/0019* (2013.01); *A61K 9/127* (2013.01); *A61K 9/5031* (2013.01); *A61K 38/00* (2013.01)

(58) Field of Classification Search
None
See application file for complete search history.

(56) References Cited

FOREIGN PATENT DOCUMENTS

| WO | 2006/005268 | 1/2006 |
| WO | 2007/022557 | 3/2007 |

OTHER PUBLICATIONS

International Search Report for PCT/CU2012/000002 dated Sep. 6, 2012.

*Primary Examiner* — Amber D Steele
*Assistant Examiner* — Schuyler Milton
(74) *Attorney, Agent, or Firm* — Hoffmann & Baron, LLP

(57) ABSTRACT

The present invention comprises cyclic peptides bearing antitumor and antiangiogenic properties, as well as their corresponding pharmaceutically-suitable salts and also pharmaceutical compositions containing it. These cyclic peptides are used to prepare medicines for human and/or veterinary therapeutics, and additionally in diagnosis. These compounds can be used to detect, monitor and/or control a range of cellular proliferation-related disorders, such as oncological diseases and undesired angiogenesis. Moreover, they can be included as part of controlled release systems, and used more precisely in the field of nanobiotechnology, either because of their self-assembly capacity or as part of other systems.

21 Claims, 8 Drawing Sheets

A

B  C

A

B  C

```
                        SEQUENCE LISTING

<160> NUMBER OF SEQ ID NOS: 76

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (1)..(9)
<223> OTHER INFORMATION: Disulfide bridge between C1 and C9

<400> SEQUENCE: 1

Cys Asn Thr Gly Arg Asp Phe Leu Cys
 1               5

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (9)..(17)
<223> OTHER INFORMATION: Disulfide bridge between C9 and C17

<400> SEQUENCE: 2

Gly Asp Thr Val Tyr Gly Phe Asn Cys Asn Thr Gly Arg Asp Phe Leu
 1               5                  10                  15
```

Cys Thr Thr Ser
            20

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (5)..(16)
<223> OTHER INFORMATION: Disulfide brdge between C5 and C16

<400> SEQUENCE: 3

Gly Asp Thr Val Cys Gly Phe Asn Ser Asn Thr Gly Arg Asp Phe Cys
 1               5                  10                  15

Ser Thr Thr Ser
            20

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (7)..(20)
<223> OTHER INFORMATION: Disulfide bridge between C7 and C20

<400> SEQUENCE: 4

Gly Asp Thr Val Tyr Gly Cys Asn Ser Asn Thr Gly Arg Asp Phe Leu
 1               5                  10                  15

Ser Thr Gly Cys
            20

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: BINDING
<222> LOCATION: (9)..(17)
<223> OTHER INFORMATION: Amide bond between K9 and D17 side chains

<400> SEQUENCE: 5

Gly Asp Thr Val Tyr Gly Phe Asn Lys Asn Thr Gly Arg Asp Phe Leu
 1               5                  10                  15

Asp Thr Thr Ser
            20

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: BINDING
<222> LOCATION: (9)..(17)
<223> OTHER INFORMATION: Amide bond between K9 and E17 side chain -continued

```
<400> SEQUENCE: 6

Gly Asp Thr Val Tyr Gly Phe Asn Lys Asn Thr Gly Arg Asp Phe Leu
1               5                   10                  15

Glu Thr Thr Ser
            20

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: BINDING
<222> LOCATION: (9)..(17)
<223> OTHER INFORMATION: Amide bond between D9 and K17 side chain

<400> SEQUENCE: 7

Gly Asp Thr Val Tyr Gly Phe Asn Asp Asn Thr Gly Arg Asp Phe Leu
1               5                   10                  15

Lys Thr Thr Ser
            20

<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: BINDING
<222> LOCATION: (9)..(17)
<223> OTHER INFORMATION: Amide bond between E9 and K17 side chains

<400> SEQUENCE: 8

Gly Asp Thr Val Tyr Gly Phe Asn Glu Asn Thr Gly Arg Asp Phe Leu
1               5                   10                  15

Lys Thr Thr Ser
            20

<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: BINDING
<222> LOCATION: (5)..(16)
<223> OTHER INFORMATION: Amide bond between K5 and D16 side chain

<400> SEQUENCE: 9

Gly Asp Thr Val Lys Gly Phe Asn Ser Asn Thr Gly Arg Asp Phe Asp
1               5                   10                  15

Ser Thr Thr Ser
            20

<210> SEQ ID NO 10
<211> LENGTH: 20
<212> TYPE: PRT
<213> ORGANISM: Artificial Sequence
<220> FEATURE:
<223> OTHER INFORMATION: Description of Artificial Sequence:synthetic
      peptide
```

```
<220> FEATURE:
<221> NAME/KEY: BINDING
<222> LOCATION: (5)..(16)
<223> OTHER INFORMATION: Amide bond between K5 and E16 side chains

<400> SEQUENCE: 10

Gly Asp Thr Val Lys Gly Phe Asn Ser Asn Thr Gly Arg Asp Phe Glu
 1               5                  10                  15

Ser Thr Thr Ser
            20

<210> SEQ ID NO 11
<211> LENGTH: 20
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: BINDING
<222> LOCATION: (5)..(16)
<223> OTHER INFORMATION: Amide bond between D5 and K16 side chain

<400> SEQUENCE: 11

Gly Asp Thr Val Asp Gly Phe Asn Ser Asn Thr Gly Arg Asp Phe Lys
 1               5                  10                  15

Ser Thr Thr Ser
            20

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: BINDING
<222> LOCATION: (5)..(16)
<223> OTHER INFORMATION: Amide bond between E5 and K16 side chains

<400> SEQUENCE: 12

Gly Asp Thr Val Glu Gly Phe Asn Ser Asn Thr Gly Arg Asp Phe Lys
 1               5                  10                  15

Ser Thr Thr Ser
            20

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: BINDING
<222> LOCATION: (7)..(20)
<223> OTHER INFORMATION: Amide bond between K7 and D20 side chains

<400> SEQUENCE: 13

Gly Asp Thr Val Tyr Gly Lys Asn Ser Asn Thr Gly Arg Asp Phe Leu
 1               5                  10                  15

Ser Thr Gly Asp
            20

<210> SEQ ID NO 14
<211> LENGTH: 20
```

```
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: BINDING
<222> LOCATION: (7)..(20)
<223> OTHER INFORMATION: Amide bond between K7 and E20 side chains

<400> SEQUENCE: 14

Gly Asp Thr Val Tyr Gly Lys Asn Ser Asn Thr Gly Arg Asp Phe Leu
 1               5                  10                  15

Ser Thr Gly Glu
            20

<210> SEQ ID NO 15
<211> LENGTH: 20
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: BINDING
<222> LOCATION: (7)..(20)
<223> OTHER INFORMATION: Amide bond between D7 and K20 side chains

<400> SEQUENCE: 15

Gly Asp Thr Val Tyr Gly Asp Asn Ser Asn Thr Gly Arg Asp Phe Leu
 1               5                  10                  15

Ser Thr Gly Lys
            20

<210> SEQ ID NO 16
<211> LENGTH: 20
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: BINDING
<222> LOCATION: (7)..(20)
<223> OTHER INFORMATION: Amide bond between E7 and K20 side chains

<400> SEQUENCE: 16

Gly Asp Thr Val Tyr Gly Glu Asn Ser Asn Thr Gly Arg Asp Phe Leu
 1               5                  10                  15

Ser Thr Gly Lys
            20

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (7)..(20)
<223> OTHER INFORMATION: Disulfide bridge between C7 and C20
<220> FEATURE:
<221> NAME/KEY: SITE
<222> LOCATION: (12)
<223> OTHER INFORMATION: D-Ala

<400> SEQUENCE: 17
```

Gly Asp Thr Val Tyr Gly Cys Asn Ser Asn Thr Ala Arg Asp Phe Leu
 1               5                  10                  15

Ser Thr Gly Cys
            20

<210> SEQ ID NO 18
<211> LENGTH: 21
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (7)..(21)
<223> OTHER INFORMATION: Disulfide bridge between C7 and C21

<400> SEQUENCE: 18

Gly Asp Thr Val Tyr Gly Cys Asn Ser Asn Thr Gly Arg Asp Phe Leu
 1               5                  10                  15

Ser Thr Thr Ser Cys
            20

<210> SEQ ID NO 19
<211> LENGTH: 21
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: BINDING
<222> LOCATION: (7)..(21)
<223> OTHER INFORMATION: Amide bond between K7 and D21 side chains

<400> SEQUENCE: 19

Gly Asp Thr Val Tyr Gly Lys Asn Ser Asn Thr Gly Arg Asp Phe Leu
 1               5                  10                  15

Ser Thr Thr Ser Asp
            20

<210> SEQ ID NO 20
<211> LENGTH: 21
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: BINDING
<222> LOCATION: (7)..(21)
<223> OTHER INFORMATION: Amide bond between K7 and E21 side chains

<400> SEQUENCE: 20

Gly Asp Thr Val Tyr Gly Lys Asn Ser Asn Thr Gly Arg Asp Phe Leu
 1               5                  10                  15

Ser Thr Thr Ser Glu
            20

<210> SEQ ID NO 21
<211> LENGTH: 21
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: BINDING

```
<222> LOCATION: (7)..(21)
<223> OTHER INFORMATION: Amide bond between D7 and K21 side chains

<400> SEQUENCE: 21

Gly Asp Thr Val Tyr Gly Asp Asn Ser Asn Thr Gly Arg Asp Phe Leu
1               5                   10                  15

Ser Thr Thr Ser Lys
            20

<210> SEQ ID NO 22
<211> LENGTH: 21
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: BINDING
<222> LOCATION: (7)..(21)
<223> OTHER INFORMATION: Amide bond between E7 and K21 side chains

<400> SEQUENCE: 22

Gly Asp Thr Val Tyr Gly Glu Asn Ser Asn Thr Gly Arg Asp Phe Leu
1               5                   10                  15

Ser Thr Thr Ser Lys
            20

<210> SEQ ID NO 23
<211> LENGTH: 21
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (7)..(21)
<223> OTHER INFORMATION: Disulfide bridge between C7 and C21
<220> FEATURE:
<221> NAME/KEY: SITE
<222> LOCATION: (12)
<223> OTHER INFORMATION: D-Ala

<400> SEQUENCE: 23

Gly Asp Thr Val Tyr Gly Cys Asn Ser Asn Thr Ala Arg Asp Phe Leu
1               5                   10                  15

Ser Thr Thr Ser Cys
            20

<210> SEQ ID NO 24
<211> LENGTH: 21
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (7)..(20)
<223> OTHER INFORMATION: Disulfide bridge between C7 and C20

<400> SEQUENCE: 24

Gly Asp Thr Val Tyr Gly Cys Asn Ser Asn Thr Gly Arg Asp Phe Leu
1               5                   10                  15

Ser Thr Gly Cys Lys
            20
```

```
<210> SEQ ID NO 25
<211> LENGTH: 21
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (7)..(20)
<223> OTHER INFORMATION: Disulfide bridge between C7 and C20
<220> FEATURE:
<221> NAME/KEY: SITE
<222> LOCATION: (12)
<223> OTHER INFORMATION: D-Ala

<400> SEQUENCE: 25

Gly Asp Thr Val Tyr Gly Cys Asn Ser Asn Thr Ala Arg Asp Phe Leu
 1               5                  10                  15

Ser Thr Gly Cys Lys
            20

<210> SEQ ID NO 26
<211> LENGTH: 22
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (7)..(21)
<223> OTHER INFORMATION: Disulfide bridge between C7 and C21

<400> SEQUENCE: 26

Gly Asp Thr Val Tyr Gly Cys Asn Ser Asn Thr Gly Arg Asp Phe Leu
 1               5                  10                  15

Ser Thr Thr Ser Cys Lys
            20

<210> SEQ ID NO 27
<211> LENGTH: 22
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (7)..(21)
<223> OTHER INFORMATION: Disulfide bridge between C7 and C21
<220> FEATURE:
<221> NAME/KEY: SITE
<222> LOCATION: (12)
<223> OTHER INFORMATION: D-Ala

<400> SEQUENCE: 27

Gly Asp Thr Val Tyr Gly Cys Asn Ser Asn Thr Ala Arg Asp Phe Leu
 1               5                  10                  15

Ser Thr Thr Ser Cys Lys
            20

<210> SEQ ID NO 28
<211> LENGTH: 20
<212> TYPE: PRT
<213> ORGANISM: Artificial Sequence
<220> FEATURE:
<223> OTHER INFORMATION: Description of Artificial Sequence:synthetic
      peptide
<220> FEATURE:
```

```
<221> NAME/KEY: DISULFID
<222> LOCATION: (7)..(20)
<223> OTHER INFORMATION: Disulfide bridge between C7 and C20
<220> FEATURE:
<221> NAME/KEY: SITE
<222> LOCATION: (6)
<223> OTHER INFORMATION: D-Ala
<220> FEATURE:
<221> NAME/KEY: SITE
<222> LOCATION: (12)
<223> OTHER INFORMATION: D-Ala

<400> SEQUENCE: 28

Gly Asp Thr Val Tyr Ala Cys Asn Ser Asn Thr Ala Arg Asp Phe Leu
 1               5                  10                  15

Ser Thr Gly Cys
            20

<210> SEQ ID NO 29
<211> LENGTH: 21
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (7)..(20)
<223> OTHER INFORMATION: Disulfide bridge between C7 and C20
<220> FEATURE:
<221> NAME/KEY: SITE
<222> LOCATION: (6)
<223> OTHER INFORMATION: D-Ala
<220> FEATURE:
<221> NAME/KEY: SITE
<222> LOCATION: (12)
<223> OTHER INFORMATION: D-Ala

<400> SEQUENCE: 29

Gly Asp Thr Val Tyr Ala Cys Asn Ser Asn Thr Ala Arg Asp Phe Leu
 1               5                  10                  15

Ser Thr Gly Cys Lys
            20

<210> SEQ ID NO 30
<211> LENGTH: 21
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (7)..(21)
<223> OTHER INFORMATION: Disulfide bridge between C7 and C21
<220> FEATURE:
<221> NAME/KEY: SITE
<222> LOCATION: (6)
<223> OTHER INFORMATION: D-Ala
<220> FEATURE:
<221> NAME/KEY: SITE
<222> LOCATION: (12)
<223> OTHER INFORMATION: D-Ala

<400> SEQUENCE: 30

Gly Asp Thr Val Tyr Ala Cys Asn Ser Asn Thr Ala Arg Asp Phe Leu
 1               5                  10                  15

Ser Thr Thr Ser Cys
            20
```

```
<210> SEQ ID NO 31
<211> LENGTH: 22
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (7)..(21)
<223> OTHER INFORMATION: Disulfide bridge between C7 and C21
<220> FEATURE:
<221> NAME/KEY: SITE
<222> LOCATION: (6)
<223> OTHER INFORMATION: D-Ala
<220> FEATURE:
<221> NAME/KEY: SITE
<222> LOCATION: (12)
<223> OTHER INFORMATION: D-Ala

<400> SEQUENCE: 31

Gly Asp Thr Val Tyr Ala Cys Asn Ser Asn Thr Ala Arg Asp Phe Leu
  1               5                  10                  15

Ser Thr Thr Ser Cys Lys
                 20

<210> SEQ ID NO 32
<211> LENGTH: 20
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: BINDING
<222> LOCATION: (7)..(20)
<223> OTHER INFORMATION: Amide bond between K7 side chain and the N20
      carboxyl terminus

<400> SEQUENCE: 32

Gly Asp Thr Val Tyr Gly Lys Asn Ser Asn Thr Gly Arg Asp Phe Leu
  1               5                  10                  15

Ser Thr Thr Asn
            20

<210> SEQ ID NO 33
<211> LENGTH: 20
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: BINDING
<222> LOCATION: (7)..(20)
<223> OTHER INFORMATION: Amide bond between the K7 side chain and the
      S20 carboxyl terminus

<400> SEQUENCE: 33

Gly Asp Thr Val Tyr Gly Lys Asn Ser Asn Thr Gly Arg Asp Phe Leu
  1               5                  10                  15

Ser Thr Thr Ser
            20

<210> SEQ ID NO 34
<211> LENGTH: 20
<212> TYPE: PRT
<213> ORGANISM: Artificial Sequence
<220> FEATURE:
<223> OTHER INFORMATION: Description of Artificial Sequence:synthetic
```

```
                                  peptide
<220> FEATURE:
<221> NAME/KEY: DISULFID
<222> LOCATION: (7)..(20)
<223> OTHER INFORMATION: Disulfide bridge between C7 and C20
<220> FEATURE:
<221> NAME/KEY: MOD_RES
<222> LOCATION: (1)
<223> OTHER INFORMATION: amino terminus of G1 is pegylated

<400> SEQUENCE: 34

Gly Asp Thr Val Tyr Gly Cys Asn Ser Asn Thr Gly Arg Asp Phe Leu
 1               5                  10                  15

Ser Thr Gly Cys
            20

<210> SEQ ID NO 35
<211> LENGTH: 21
<212> TYPE: PRT
<213> ORGANISM: Artificial Sequence
<220> FEATURE:
<223> OTHER INFORMATION: Description of Artificial Sequence:synthetic
                                  peptide
<220> FEATURE:
<221> NAME/KEY: DISULFID
<222> LOCATION: (7)..(20)
<223> OTHER INFORMATION: Disulfide bridge between C7 and C20

<400> SEQUENCE: 35

Gly Asp Thr Val Tyr Gly Cys Asn Ser Asn Thr Gly Arg Asp Phe Leu
 1               5                  10                  15

Ser Thr Gly Cys Gln
            20

<210> SEQ ID NO 36
<211> LENGTH: 21
<212> TYPE: PRT
<213> ORGANISM: Artificial Sequence
<220> FEATURE:
<223> OTHER INFORMATION: Description of Artificial Sequence:synthetic
                                  peptide
<220> FEATURE:
<221> NAME/KEY: DISULFID
<222> LOCATION: (7)..(20)
<223> OTHER INFORMATION: Disulfide bridge between C7 and C20

<400> SEQUENCE: 36

Gly Asp Thr Val Tyr Gly Cys Asn Ser Asn Thr Gly Arg Asp Phe Leu
 1               5                  10                  15

Ser Thr Gly Cys Asn
            20

<210> SEQ ID NO 37
<211> LENGTH: 21
<212> TYPE: PRT
<213> ORGANISM: Artificial Sequence
<220> FEATURE:
<223> OTHER INFORMATION: Description of Artificial Sequence:synthetic
                                  peptide
<220> FEATURE:
<221> NAME/KEY: DISULFID
<222> LOCATION: (7)..(20)
<223> OTHER INFORMATION: Disulfide bridge between C7 and C20

<400> SEQUENCE: 37

Gly Asp Thr Val Tyr Gly Cys Asn Ser Asn Thr Gly Arg Asp Phe Leu
 1               5                  10                  15

Ser Thr Gly Cys Arg
```

```
<210> SEQ ID NO 38
<211> LENGTH: 22
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (7)..(21)
<223> OTHER INFORMATION: Disulfide bridge between C7 and C21

<400> SEQUENCE: 38

Gly Asp Thr Val Tyr Gly Cys Asn Ser Asn Thr Gly Arg Asp Phe Leu
 1               5                  10                  15

Ser Thr Thr Ser Cys Gln
             20

<210> SEQ ID NO 39
<211> LENGTH: 22
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (7)..(21)
<223> OTHER INFORMATION: Disulfide bridge between C7 and C21

<400> SEQUENCE: 39

Gly Asp Thr Val Tyr Gly Cys Asn Ser Asn Thr Gly Arg Asp Phe Leu
 1               5                  10                  15

Ser Thr Thr Ser Cys Asn
             20

<210> SEQ ID NO 40
<211> LENGTH: 22
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (7)..(21)
<223> OTHER INFORMATION: Disulfide bridge between C7 and C21

<400> SEQUENCE: 40

Gly Asp Thr Val Tyr Gly Cys Asn Ser Asn Thr Gly Arg Asp Phe Leu
 1               5                  10                  15

Ser Thr Thr Ser Cys Arg
             20

<210> SEQ ID NO 41
<211> LENGTH: 22
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: BINDING
<222> LOCATION: (7)..(21)
<223> OTHER INFORMATION: Amide bond between K7 and E21 side chains

<400> SEQUENCE: 41
```

```
Gly Asp Thr Val Tyr Gly Lys Asn Ser Asn Thr Gly Arg Asp Phe Leu
1               5                   10                  15

Ser Thr Thr Ser Glu Lys
                20

<210> SEQ ID NO 42
<211> LENGTH: 22
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: BINDING
<222> LOCATION: (7)..(21)
<223> OTHER INFORMATION: Amide bonds between K7 and E21 side chains

<400> SEQUENCE: 42

Gly Asp Thr Val Tyr Gly Lys Asn Ser Asn Thr Gly Arg Asp Phe Leu
1               5                   10                  15

Ser Thr Thr Ser Glu Gln
                20

<210> SEQ ID NO 43
<211> LENGTH: 22
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: BINDING
<222> LOCATION: (7)..(21)
<223> OTHER INFORMATION: Amide bond between K7 and E21 side chains

<400> SEQUENCE: 43

Gly Asp Thr Val Tyr Gly Lys Asn Ser Asn Thr Gly Arg Asp Phe Leu
1               5                   10                  15

Ser Thr Thr Ser Glu Asn
                20

<210> SEQ ID NO 44
<211> LENGTH: 22
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: BINDING
<222> LOCATION: (7)..(21)
<223> OTHER INFORMATION: Amide bond between K7 and E21 side chains

<400> SEQUENCE: 44

Gly Asp Thr Val Tyr Gly Lys Asn Ser Asn Thr Gly Arg Asp Phe Leu
1               5                   10                  15

Ser Thr Thr Ser Glu Arg
                20

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence:synthetic
      peptide
<220> FEATURE:
```

```
<221> NAME/KEY: DISULFID
<222> LOCATION: (1)..(9)
<223> OTHER INFORMATION: Disulfide bridge between C1 and C9
<220> FEATURE:
<221> NAME/KEY: SITE
<222> LOCATION: (4)
<223> OTHER INFORMATION: D-ala

<400> SEQUENCE: 45

Cys Asn Thr Ala Arg Asp Phe Leu Cys
 1               5

<210> SEQ ID NO 46
<211> LENGTH: 20
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (7)..(20)
<223> OTHER INFORMATION: Disulfide bridge between C7 and C20
<220> FEATURE:
<221> NAME/KEY: SITE
<222> LOCATION: (6)
<223> OTHER INFORMATION: D-Ala
<220> FEATURE:
<221> NAME/KEY: SITE
<222> LOCATION: (8)
<223> OTHER INFORMATION: D-Gln
<220> FEATURE:
<221> NAME/KEY: SITE
<222> LOCATION: (12)
<223> OTHER INFORMATION: D-Ala

<400> SEQUENCE: 46

Gly Asp Thr Val Tyr Ala Cys Gln Ser Asn Thr Ala Arg Asp Phe Leu
 1               5                  10                  15

Ser Thr Gly Cys
            20

<210> SEQ ID NO 47
<211> LENGTH: 21
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (7)..(20)
<223> OTHER INFORMATION: Disulfide bridge between C7 and C20
<220> FEATURE:
<221> NAME/KEY: SITE
<222> LOCATION: (6)
<223> OTHER INFORMATION: D-Ala
<220> FEATURE:
<221> NAME/KEY: SITE
<222> LOCATION: (8)
<223> OTHER INFORMATION: D-Gln
<220> FEATURE:
<221> NAME/KEY: SITE
<222> LOCATION: (12)
<223> OTHER INFORMATION: D-Ala

<400> SEQUENCE: 47

Gly Asp Thr Val Tyr Ala Cys Gln Ser Asn Thr Ala Arg Asp Phe Leu
 1               5                  10                  15

Ser Thr Gly Cys Lys
            20
```

```
<210> SEQ ID NO 48
<211> LENGTH: 21
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (7)..(21)
<223> OTHER INFORMATION: Disulfide bridge between C7 and C21
<220> FEATURE:
<221> NAME/KEY: SITE
<222> LOCATION: (6)
<223> OTHER INFORMATION: D-Ala
<220> FEATURE:
<221> NAME/KEY: SITE
<222> LOCATION: (8)
<223> OTHER INFORMATION: D-Gln
<220> FEATURE:
<221> NAME/KEY: SITE
<222> LOCATION: (12)
<223> OTHER INFORMATION: D-Ala

<400> SEQUENCE: 48

Gly Asp Thr Val Tyr Ala Cys Gln Ser Asn Thr Ala Arg Asp Phe Leu
 1               5                  10                  15

Ser Thr Thr Ser Cys
            20

<210> SEQ ID NO 49
<211> LENGTH: 22
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (7)..(21)
<223> OTHER INFORMATION: Disulfide bridge between C7 and C21
<220> FEATURE:
<221> NAME/KEY: SITE
<222> LOCATION: (6)
<223> OTHER INFORMATION: D-Ala
<220> FEATURE:
<221> NAME/KEY: SITE
<222> LOCATION: (8)
<223> OTHER INFORMATION: D-Gln
<220> FEATURE:
<221> NAME/KEY: SITE
<222> LOCATION: (12)
<223> OTHER INFORMATION: D-Ala

<400> SEQUENCE: 49

Gly Asp Thr Val Tyr Ala Cys Gln Ser Asn Thr Ala Arg Asp Phe Leu
 1               5                  10                  15

Ser Thr Thr Ser Cys Lys
            20

<210> SEQ ID NO 50
<211> LENGTH: 21
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (9)..(17)
<223> OTHER INFORMATION: Disulfide bridge between C9 and C17
<220> FEATURE:
```

```
<221> NAME/KEY: SITE
<222> LOCATION: (6)
<223> OTHER INFORMATION: D-Ala
<220> FEATURE:
<221> NAME/KEY: SITE
<222> LOCATION: (8)
<223> OTHER INFORMATION: D-Gln
<220> FEATURE:
<221> NAME/KEY: SITE
<222> LOCATION: (12)
<223> OTHER INFORMATION: D-Ala

<400> SEQUENCE: 50

Gly Asp Thr Val Tyr Ala Phe Gln Cys Asn Thr Ala Arg Asp Phe Leu
 1               5                  10                  15

Cys Thr Thr Ser Lys
             20

<210> SEQ ID NO 51
<211> LENGTH: 20
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (5)..(16)
<223> OTHER INFORMATION: Disulfide bridge between C5 and C16
<220> FEATURE:
<221> NAME/KEY: SITE
<222> LOCATION: (6)
<223> OTHER INFORMATION: D-Ala
<220> FEATURE:
<221> NAME/KEY: SITE
<222> LOCATION: (8)
<223> OTHER INFORMATION: D-Gln
<220> FEATURE:
<221> NAME/KEY: SITE
<222> LOCATION: (12)
<223> OTHER INFORMATION: D-Ala

<400> SEQUENCE: 51

Gly Asp Thr Val Cys Ala Phe Gln Ser Asn Thr Ala Arg Asp Phe Cys
 1               5                  10                  15

Ser Thr Thr Ser
             20

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (2)..(10)
<223> OTHER INFORMATION: Disulfide bridge between C2 and C10
<220> FEATURE:
<221> NAME/KEY: LIPID
<222> LOCATION: (1)
<223> OTHER INFORMATION: G1 is lipidated

<400> SEQUENCE: 52

Gly Cys Asn Thr Gly Arg Asp Phe Leu Cys
 1               5                  10

<210> SEQ ID NO 53
<211> LENGTH: 10
<212> TYPE: PRT
```

```
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (1)..(9)
<223> OTHER INFORMATION: Disulfide bridge between C1 and C9
<220> FEATURE:
<221> NAME/KEY: LIPID
<222> LOCATION: (10)
<223> OTHER INFORMATION: G10 is lipidated

<400> SEQUENCE: 53

Cys Asn Thr Gly Arg Asp Phe Leu Cys Gly
 1               5                  10

<210> SEQ ID NO 54
<211> LENGTH: 20
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (7)..(20)
<223> OTHER INFORMATION: Disulfide bridge between C7 and C20

<400> SEQUENCE: 54

Gly Asp Thr Val Tyr Gly Cys Asn Ser Asn Thr Gly Arg Asp Phe Leu
 1               5                  10                  15

Ser Thr Ala Cys
            20

<210> SEQ ID NO 55
<211> LENGTH: 21
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (7)..(20)
<223> OTHER INFORMATION: Disulfide bridge between C7 and C20

<400> SEQUENCE: 55

Gly Asp Thr Val Tyr Gly Cys Asn Ser Asn Thr Gly Arg Asp Phe Leu
 1               5                  10                  15

Ser Thr Ala Cys Gln
            20

<210> SEQ ID NO 56
<211> LENGTH: 21
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (7)..(20)
<223> OTHER INFORMATION: Disulfide bridge between C7 and C20

<400> SEQUENCE: 56

Gly Asp Thr Val Tyr Gly Cys Asn Ser Asn Thr Gly Arg Asp Phe Leu
 1               5                  10                  15

Ser Thr Ala Cys Asn
```

<210> SEQ ID NO 57
<211> LENGTH: 21
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (7)..(20)
<223> OTHER INFORMATION: Disulfide bridge between C7 and C20

<400> SEQUENCE: 57

Gly Asp Thr Val Tyr Gly Cys Asn Ser Asn Thr Gly Arg Asp Phe Leu
 1               5                  10                  15

Ser Thr Ala Cys Arg
             20

<210> SEQ ID NO 58
<211> LENGTH: 21
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (7)..(20)
<223> OTHER INFORMATION: Disulfide bridge between C7 and C20

<400> SEQUENCE: 58

Gly Asp Thr Val Tyr Gly Cys Asn Ser Asn Thr Gly Arg Asp Phe Leu
 1               5                  10                  15

Ser Thr Ala Cys Lys
             20

<210> SEQ ID NO 59
<211> LENGTH: 20
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (7)..(20)
<223> OTHER INFORMATION: Disulfide bridge between C7 and C20

<400> SEQUENCE: 59

Gly Asp Thr Val Tyr Gly Cys Asn Ser Asn Thr Gly Arg Asp Phe Leu
 1               5                  10                  15

Ser Thr Thr Cys
             20

<210> SEQ ID NO 60
<211> LENGTH: 21
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (8)..(21)
<223> OTHER INFORMATION: Disulfide bridge between C8 and C21
<220> FEATURE:
<221> NAME/KEY: SITE -continued

```
<222> LOCATION: (1)
<223> OTHER INFORMATION: E1 is a pyroglutamic acid

<400> SEQUENCE: 60

Glu Gly Asp Thr Val Tyr Gly Cys Asn Ser Asn Thr Gly Arg Asp Phe
 1               5                  10                  15

Leu Ser Thr Gly Cys
             20

<210> SEQ ID NO 61
<211> LENGTH: 20
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (7)..(20)
<223> OTHER INFORMATION: Disulfide bridge between C7 and C20
<220> FEATURE:
<221> NAME/KEY: MOD_RES
<222> LOCATION: (1)
<223> OTHER INFORMATION: ACETYLATION

<400> SEQUENCE: 61

Gly Asp Thr Val Tyr Gly Cys Asn Ser Asn Thr Gly Arg Asp Phe Leu
 1               5                  10                  15

Ser Thr Gly Cys
             20

<210> SEQ ID NO 62
<211> LENGTH: 20
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (7)..(20)
<223> OTHER INFORMATION: Disulfide bridge between C7 and C20
<220> FEATURE:
<221> NAME/KEY: MOD_RES
<222> LOCATION: (1)
<223> OTHER INFORMATION: amino terminus of G1 is pegylated
<220> FEATURE:
<221> NAME/KEY: MOD_RES
<222> LOCATION: (20)
<223> OTHER INFORMATION: carboxyl terminus of C20 is pegylated

<400> SEQUENCE: 62

Gly Asp Thr Val Tyr Gly Cys Asn Ser Asn Thr Gly Arg Asp Phe Leu
 1               5                  10                  15

Ser Thr Gly Cys
             20

<210> SEQ ID NO 63
<211> LENGTH: 21
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (8)..(21)
<223> OTHER INFORMATION: Disulfide bridge between C8 and C21
<220> FEATURE:
<221> NAME/KEY: MOD_RES
```

<222> LOCATION: (21)
<223> OTHER INFORMATION: pegylation on the carboxyl terminus

<400> SEQUENCE: 63

Asn Gly Asp Thr Val Tyr Gly Cys Asn Ser Asn Thr Gly Arg Asp Phe
 1               5                  10                  15

Leu Ser Thr Gly Cys
            20

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: BINDING
<222> LOCATION: (1)..(11)
<223> OTHER INFORMATION: Amide bond between the amino and carboxyl
      groups of the main chain of amino and carboxyl termini residues
<220> FEATURE:
<221> NAME/KEY: SITE
<222> LOCATION: (2)
<223> OTHER INFORMATION: D-Ser

<400> SEQUENCE: 64

Leu Ser Pro Thr Pro Asn Thr Gly Arg Asp Phe
 1               5                  10

<210> SEQ ID NO 65
<211> LENGTH: 11
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: BINDING
<222> LOCATION: (1)..(11)
<223> OTHER INFORMATION: Amide bond between the amino and carboxyl
      groups of the main chain of amino and carboxyl termini residues
<220> FEATURE:
<221> NAME/KEY: SITE
<222> LOCATION: (2)
<223> OTHER INFORMATION: D-Ser
<220> FEATURE:
<221> NAME/KEY: SITE
<222> LOCATION: (8)
<223> OTHER INFORMATION: D-Ala

<400> SEQUENCE: 65

Leu Ser Pro Thr Pro Asn Thr Ala Arg Asp Phe
 1               5                  10

<210> SEQ ID NO 66
<211> LENGTH: 20
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: DISULFID
<222> LOCATION: (7)..(20)
<223> OTHER INFORMATION: Disulfide bridge between C7 and C20
<220> FEATURE:
<221> NAME/KEY: SITE
<222> LOCATION: (1)
<223> OTHER INFORMATION: D-Ala

<400> SEQUENCE: 66

```
Ala Asp Thr Val Tyr Gly Cys Asn Ser Asn Thr Gly Arg Asp Phe Leu
 1               5                  10                  15

Ser Thr Gly Cys
            20

<210> SEQ ID NO 67
<211> LENGTH: 14
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: BINDING
<222> LOCATION: (1)..(14)
<223> OTHER INFORMATION: Amide bond between the amino and carboxyl
      groups of the main chain of amino and carboxyl termini residues
<220> FEATURE:
<221> NAME/KEY: SITE
<222> LOCATION: (7)
<223> OTHER INFORMATION: D-Ala

<400> SEQUENCE: 67

Asp Phe Leu Ser Thr Pro Ala Gln Asn Ser Asn Thr Gly Arg
 1               5                  10

<210> SEQ ID NO 68
<211> LENGTH: 14
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: BINDING
<222> LOCATION: (1)..(14)
<223> OTHER INFORMATION: amide bond between the amino and carboxyl
      groups of the main chain of amino and carboxyl termini residues
<220> FEATURE:
<221> NAME/KEY: SITE
<222> LOCATION: (7)
<223> OTHER INFORMATION: D-Ala

<400> SEQUENCE: 68

Asp Phe Leu Ser Arg Pro Ala Gln Asn Ser Asn Thr Gly Arg
 1               5                  10

<210> SEQ ID NO 69
<211> LENGTH: 11
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: BINDING
<222> LOCATION: (1)..(11)
<223> OTHER INFORMATION: Amide bond between the amino and carboxyl
      groups of the main chain of amino and carboxyl termini residues
<220> FEATURE:
<221> NAME/KEY: SITE
<222> LOCATION: (2)
<223> OTHER INFORMATION: D-Ala

<400> SEQUENCE: 69

Leu Ala Pro Thr Pro Asn Thr Gly Arg Asp Phe
 1               5                  10

<210> SEQ ID NO 70
<211> LENGTH: 11
```

```
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: BINDING
<222> LOCATION: (1)..(11)
<223> OTHER INFORMATION: Amide bond between the amino and carboxyl
      groups of the main chain of amino and carboxyl termini residues

<400> SEQUENCE: 70

Leu Gly Pro Thr Pro Asn Thr Gly Arg Asp Phe
 1               5                  10

<210> SEQ ID NO 71
<211> LENGTH: 14
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: BINDING
<222> LOCATION: (1)..(14)
<223> OTHER INFORMATION: Amide bond between the amino and carboxyl
      groups of the main chain of amino and carboxyl termini residues

<400> SEQUENCE: 71

Asp Phe Leu Ser Thr Pro Gly Gln Asn Ser Asn Thr Gly Arg
 1               5                  10

<210> SEQ ID NO 72
<211> LENGTH: 14
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: BINDING
<222> LOCATION: (1)..(14)
<223> OTHER INFORMATION: Amide bond between the amino and carboxyl
      groups of the main chain of amino and carboxyl termini residues

<400> SEQUENCE: 72

Asp Phe Leu Ser Arg Pro Gly Gln Asn Ser Asn Thr Gly Arg
 1               5                  10

<210> SEQ ID NO 73
<211> LENGTH: 14
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: BINDING
<222> LOCATION: (1)..(14)
<223> OTHER INFORMATION: Amide bond between the amino and carboxyl
      groups of the main chain of amino and carboxyl termini residues
<220> FEATURE:
<221> NAME/KEY: SITE
<222> LOCATION: (7)
<223> OTHER INFORMATION: D-Ala
<220> FEATURE:
<221> NAME/KEY: SITE
<222> LOCATION: (8)
<223> OTHER INFORMATION: Q8 is L-b-methylglutamine
<220> FEATURE:
<221> NAME/KEY: SITE
<222> LOCATION: (9)
<223> OTHER INFORMATION: N9 is N-methyl asparagine
```

<400> SEQUENCE: 73

Asp Phe Leu Ser Arg Pro Ala Gln Asn Ser Asn Thr Gly Arg
 1               5                  10

<210> SEQ ID NO 74
<211> LENGTH: 14
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: BINDING
<222> LOCATION: (1)..(14)
<223> OTHER INFORMATION: Amide bond between the amino and carboxyl
      groups of the main chain of amino and carboxyl termini residues
<220> FEATURE:
<221> NAME/KEY: SITE
<222> LOCATION: (7)
<223> OTHER INFORMATION: D-Ala
<220> FEATURE:
<221> NAME/KEY: SITE
<222> LOCATION: (8)
<223> OTHER INFORMATION: Q8 is L-b-methylglutamine
<220> FEATURE:
<221> NAME/KEY: SITE
<222> LOCATION: (9)
<223> OTHER INFORMATION: N9 is N-methyl asparagine

<400> SEQUENCE: 74

Asp Phe Leu Ser Thr Pro Ala Gln Asn Ser Asn Thr Gly Arg
 1               5                  10

<210> SEQ ID NO 75
<211> LENGTH: 13
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: BINDING
<222> LOCATION: (1)..(13)
<223> OTHER INFORMATION: Amide bond between the amino and carboxyl
      groups of the main chain of amino and carboxyl termini residues

<400> SEQUENCE: 75

Asp Phe Leu Ser Arg Arg Pro Asn Ser Asn Thr Gly Arg
 1               5                  10

<210> SEQ ID NO 76
<211> LENGTH: 13
<212> TYPE: PRT
<213> ORGANISM: Artificial Sequence
<220> FEATURE:
<223> OTHER INFORMATION: Description of Artificial Sequence:synthetic
      peptide
<220> FEATURE:
<221> NAME/KEY: BINDING
<222> LOCATION: (1)..(13)
<223> OTHER INFORMATION: Amide bond between the amino and carboxyl
      groups of the main chain of amino and carboxyl termini residues

<400> SEQUENCE: 76

Asp Phe Leu Ser Lys Lys Pro Asn Ser Asn Thr Gly Arg
 1               5                  10

CYCLIC PEPTIDES WITH AN ANTI-NEOPLASIC AND ANTI-ANGIOGENIC ACTIVITY

CLAIM OF PRIORITY

This application is the U.S. National Phase of, and Applicants claim priority from, International Application Number PCT/CU2012/000002 filed Mar. 21, 2012 and Cuban Patent Application No. CU 2011/0067 filed Mar. 21, 2011, which are incorporated herein by reference.

TECHNICAL FIELD

The present invention is related with the field of Biotechnology and the pharmaceutical industry, more precisely with designing and obtaining cyclic peptides intended for diagnosis and therapy of oncological diseases or any other pathologies involving undesired cellular proliferation.

BACKGROUND OF THE INVENTION

Cancer is a disease characterized by uncontrolled cellular division and growth. Cancer cells gain the capacity to invade the organ of origin, spread through the bloodstream and lymph to distal organs and establish and growth on them. That is a highly heterogeneous process, but common for over 200 types of cancers of quite varied evolution. Several genes have to be simultaneously altered for developing the disease. All these properties increase the complexity for studying and unraveling the mechanisms of malignancies, and therefore, cancer research is a wide and multidisciplinary field and involves several lines of investigation. Significantly, this disease is the second death cause in relevance worldwide and is expected to become the first one for the year 2020, even more deadly than cardiovascular diseases (Forteza F (2004) Avances médicos de Cuba. 40:33).

In fact, cancer is already the first death cause in developed countries and the second death cause in the developing ones (World Health Organization. The Global Burden of Disease: 2004 Update. Geneva: World Health Organization; 2008). Its incidence is rising in these last due to increased aging population, and even more frequently because of cancer-prone lifestyles—physical inactivity, smoking and "western" diets.

There were estimates at GLOBOCAN 2008 of 12.7 millions of patients living with cancer and 7.6 million deaths in 2008; of them, 56% of patients and 64% of deaths occurred in developing countries (Ferlay J, Shin H R, Bray F, Forman D, Mathers C D, Parkin D. GLOBOCAN 2008, Cancer Incidence and Mortality Worldwide: IARC Cancer Base No. 10. Lyon, France: International Agency for Research on Cancer; Available from: http://globocan.iarc.fr. 2010. Accessed Aug. 17, 2010).

Cancer survival tends to be far lower in developing countries, probably because of combined late diagnosis and the limited access to timely and appropriate treatment and regardless of the cytotoxic drugs already available and being optimized for cancer treatment. New biological molecules are required to create a new generation of anticancer medicines, more efficacious and safer in a near future and able to significantly permeate the market of cancer therapeutics.

Currently, it has been widely accepted that to be effective, cancer treatment have to combine different action principles, such as: direct action on tumor cells and effect on the tumor environment. This can be achieved by combining molecules separately bearing each of these properties, or simultaneously showing both of them. Undoubtedly, this last type of molecules is advantageous since the pharmacological and economical points of view. Preclinical trials with angiogenesis inhibitors intended to interrupt oxygen and nutrient supply to the tumor have shown very promising results, frequently achieving complete or partial tumor regression in the absence of resistance against the inhibitor. Up to now, the major achievement in clinical trials has been the sustained compensation of the disease for a given period of time. For that purpose, anti-angiogenic agents are being used as adjuvant therapy for other antitumorals in combination.

Results from clinical trials have shown that single targeting of angiogenesis modulators is insufficient for a sustained inhibitory response. There is an increasing demand for more effective anti-angiogenic agents able to arrest and also revert tumor growth, in order to achieve a significant increase in patient's lifespan and quality of life when compared to treatments established.

Currently available peptides represent a small fraction among the myriad of agents being used for therapeutic purposes. In fact, the potential of peptides is being improved with the aid of new technologies for modifying their structure, pharmacokinetics, biodistribution, stability and preclinical applications. Particularly, they have gained relevance in cancer therapy because of the novel methodologies available for modifying them and increasing their anticancer efficacy (Li, Zhi J.; Cho, Chi H. Current Pharmaceutical Design, 16 (10), April 2010, pp. 1180-1189).

Several studies have shown the affordability of using peptides for cancer diagnosis and therapy. Some of them are in advanced clinical phases of development, and other new generations have being appearing in the last years, with promising preclinical results.

The cytotoxic activity of a lytic peptide designed to bind the epidermal growth factor receptor was demonstrated in several human cancer cell lines. It was evidenced that conformational changes arising from binding of the lytic peptide increased its selectivity for association to the membrane of cancer cells, and this acquired synergic action resulted in a selective destruction of the tumor cells. Treatment with the lytic peptide binding the epidermal growth factor receptor exhibited cytotoxic activity in vitro against cancer cells resistant to tyrosine kinase inhibitors with K-ras mutations (Kohno, Masayuki. European Journal of Cancer 47(5), p. 773, March 2011).

Cell penetrating peptides are commonly coupled to oligonucleotides to increase their effectiveness in cancer therapy. For this purpose, cell penetrating peptides have being designed comprising a glutamate peptide linked to the N-terminus of the Oct6 NLS, which demonstrated to co-localize into the cell nucleus, and also its uptake by pancreatic and prostate cancer cell lines (Lewis, H Dan. BMC Biotechnology, 10(1), p. 79, October 2010).

A peptide fragment from the tissue factor pathway inhibitor (TFPI), which is a naturally anticoagulating protein, was able to block tumor growth and angiogenesis in in vivo models. Moreover, it inhibited tumor metastasis and the growth of new blood vessels with no apparent effect on the normal ones (HEMBROUGH Todd A.; RUIZ Jose F.; SWERDLOW Bonnie M.; SWARTZ Glenn M.; HAMMERS Hans J.; ZHANG Li; PLUM Stacy M.; WILLIAMS Mark S.; STRICKLAND Dudley K.; PRIBLUDA Victor S. Blood A. 2004, vol. 103, n° 9, pp. 3374-3380).

The development of more selective agents for imaging and treatment of different tumors is the current tendency in cancer therapy and diagnosis. In this sense, peptides are small amino acid sequences which can be obtained or designed to bind a predetermined molecular target, and they are potentially able to interfere with its function. These specific peptides can inhibit components of specific signals essential for cancer development and progression.

Serralysin is the major extracellular protein of the bacterium *Serratia marcescens* CMIB4202 and is associated to the pathogenicity of this microorganism in humans, with attributed antitumoral properties dependent on its catalytic activity (Wu Jun, Akaike T, Hayashida K, et al., (2001) Japanese J. Cancer Res. 92:439-451). In this strain (*S. marcescens* CMIB4202), the most abundant extracellular protein is the p50 protein, which belongs to the family of Serralysins (SERMA). It is known that the polypeptide comprising the C-terminal non-catalytitc domain of this serralysin (denominated p25) is a potent inhibitor of endothelial proliferation and growth of primary tumors and metastasis in vivo (Abrahantes-Pérez M C et al., "Pharmaceutical composition containing polypeptide fragments of serralysins". International Patent Application No. WO 2006/005268). This polypeptide was named CIGB370r when expressed recombinant in *Escherichia coli*.

There is a great demand on identifying and obtaining more potent antitumoral agents because of the increasing incidence of this disease, to replace or complement current cancer therapy in those patients requiring it, in spite of multiple drugs available for that purpose.

DETAILED DESCRIPTION OF THE INVENTION

This invention contributes to solve the abovementioned problems, by providing cyclic peptides with antitumoral and antiangiogenic properties. Herein, the design and generation of these peptide compounds are addressed, also demonstrating their efficacy in several cancer animal models.

Surprisingly, the antitumoral activity of the *S. marcescens* p25 polypeptide was reproduced by a structurally constrained peptide fragment which was barely exposed into the interface between the N- and C-terminal domains of Serralisine. This suggested that the structural conformation in that region of the polypeptide was the minimal functionally active structural unit of the p25 polypeptide, buried into the Serralysin and probably being exposed during the protein autocatalysis or once at the tumor proteolytic environment. Data shown inhere demonstrate that the constrained peptides of the present invention bear direct cytotoxic activity on tumor cells and antiangiogenic activity, and suggest a possible mechanism and a new paradigm for infection-mediated tumor regression.

Peptides are very flexible molecules and, as such, can adopt different structures. One or more of those possible structures could be of specific biological relevance. To determine the possible relevant conformations, it is necessary to restrain the peptides into a single region of conformational space, further determining if that is the relevant form. Ultimately, by screening several of those conformations, it is possible to find the biologically relevant ones.

There are novel methodologies to create more accurate synthetic structures. Certain flexibility must be taken into consideration. That is, if the designed structure is too rigid, another structure cannot be adopted with the properties desired for its biological activity in vivo, considering that a slightly flexible structure is capable of that adjustment. Such a valuable knowledge on the requirements to be sufficed for peptide receptors, active sites of the enzymes and a wide variety of other biological processes is provided by using the adequate techniques and methodologies for designing synthetic peptides.

Properties displayed by a peptide in the biological systems depend on the peptide structure. Hence, the ability to use rational design for generating useful peptides depends on the respective skills for establishing the specific relationships between the molecular structure and its biological activity. The skills for recognizing such relationships are supported by a several uncertainties, which arise not only from biological assay systems, but also from data interpretation. The more complex factor involved is the difficulty to determine the tridimensional structure of the peptide itself. Many peptides are inherently flexible and assume a wide range of conformations in solution. The problem resides on detecting which among all the possible conformations is responsible for the observed peptide activity, with many peptides been active in more than one conformation. The use of conformational constraints has being useful to elucidate such structure-function relationships. If the peptide is restricted to a very particular conformation or one closely resembling the family of active conformations, then the measured activity directly represents the effect of that structure. Even when an absolutely rigid molecule is impossible to be obtained, it can be started on attributing certain biological activities to its causative structures by designing the analogues, with the prescribed structural motifs.

In the present invention, the physical mapping of functional sites within the sequence of the p50/p25 protein by using synthetic peptides of 20 aa. overlapped in 10 and further seeking for in vitro cytotoxic activity on tumor cells (see Example 2) indicated that the peptide Gly255-Ser274 (N06P87) is active. Nevertheless, the in vivo activity of this peptide was lower than that displayed by the p25 protein. Additionally, the substitution of the Gly266-Asp268 segment by the Ala-Ala-Ala tripeptide both on the p25-similar CIGB370r recombinant polypeptide and in the N06P87 synthetic peptide abolished the biological activity of both molecules, indicating that this segment is essential for the anticancer activity. Moreover, this result suggests that one or more side chains are required on residues Arg267 and Asp268 for the interaction with (the) receptor(s), yet to be identified, in spite of a plausible negative effect of the triple mutation on the respective peptide and the biologically active protein conformations. In this sense, if assuming that the local, biologically relevant structure of the tripeptide is similar to that in the crystallographic structure of p50, then the substitution of Gly266 per Ala is highly unfavorable, since the main chain on this residue adopts positive torsion angles prohibitive for the alanine amino acid (FIG. 14). In addition, results shown in Example 2 evidence that the presence of the Gly266-Asp268 fragment per se is insufficient to achieve the biological effect and other residues are also required. As shown in Table 2, the synthetic peptide F07P16, comprising the sequence Thr265-Trp284 and overlapped in 10 residues with the linear peptide N06P87 (Gly255-Ser274), is inactive, in spite of bearing the Gly266-Asp268 sequence.

In the present invention, is surprising the identification of the Gly255-Ser274 as part of a functional site responsible for the anticancer activity of the p50/p25, due to the cryptic nature of that segment within the 3D structure of the p50 protein. Most amino acids on the Gly255-Ser274 segment are completely or partially occluded within the 3D structure of the p50 protein, including residues Thr257, Tyr258, Gly259, Phe260, Thr265, Arg267, Phe269, Leu270 and Thr272. The turn Arg267-Leu270 is part of the interface surface between the N- and C-terminal domains of the protein. Residues Arg267 and Asp268 form salt bridges (double hydrogen bridges each) with the N-terminal domain residues Asp98 and Arg171, respectively. The interface also comprises the hydrophobic inter-domain interactions involving the Phe269 residue in the C-terminal domain and the Ala232 and Ala233 residues in the N-terminal domain. Additionally, the cryptic nature of the site is consistent with the higher potency of the p25 protein compared to that of p50, since p25 lacks the N-terminal domain and its Gly255-Ser274 segment is more exposed (see Example 3, FIG. 5 and Table 3).

In the present invention it was evidenced that the conformation of the N06P87 peptide is essential for its biological activity. The relevance of the N03P87 peptide conformation on its biological activity is supported by the results in Example 4, showing that its activity depends on the flanking regions which guarantee the proper folding of the molecule. On the other hand, the p25 polypeptide showed no activity when expressed recombinant and after renaturation in the absence of calcium. Hence, the unfolded preparations corresponding to polypeptides lacking calcium atoms have no activity (calcium binding is required for the proper protein folding and stabilization). Additionally in Example 4, it is shown that the introduction of a disulfide bridge in the N06P87 peptide—by adding a cysteine residue at the N-terminus and another at the C-terminus—promotes the loss of peptide's biological activity (peptide N06P89 in Table 4, FIG. 7). Cyclization introduced by these means reduces the conformational space accessible for the peptide in solution; nevertheless, cyclization is incompatible with the conformation adopted by the Gly255-Ser274 segment in the p50 folded structure. The distance between the amine and carboxyl termini of the Gly255-Ser274 segment on the crystallographic structure of the protein is 24.4 Å long (FIG. 10E), which is incompatible with the disulfide bridge stereo-chemistry (alpha carbon-alpha carbon distance between coupled cysteines never longer than 7 Å). This modification, therefore, presupposes a significant alteration in the structural properties of the peptide chain in N06P87. These results and their respective analyses suggest that the N06P87 active conformation could be similar to that of the Gly255-Ser274 segment in the native p25 polypeptide.

As shown in examples 2, 4 and 6, it is feasible to design peptide analogues resembling the biological activity of the p25 polypeptide. In this invention is presented the design of a family of potent short- and medium-sized peptides (9 to 25 residues-long) based on the structure of the N06P87 peptide, and modified by means of introducing/substituting certain chemical groups and/or structural restrictions (Table 5), which allow these peptides to show efficacy and potency values similar or even better than those of the p25 polypeptide.

Besides their efficacy and potency, the short- and medium-sized peptides of the present invention have several advantages as anticancer agents, compared to the native complete proteins. Generally, the size of the molecule influences the pharmacokinetic properties of anticancer agents (such as biodistribution). Well documented examples are recombinant single chain antibodies (r-sc-Fv) when compared to their respective antibodies, the former displaying better access to tissues and tumors, hardly accessible to complete antibodies (Cortez-Retamozo V, Backmann N, Senter P D, Wernery U, De Baetselier P, Muyldermans S, Revets H; (2004). Cancer Res. 64(8):2853-7).

Antibody therapies have had a particularly limited impact on the treatment of solid tumors (Stern M, Herrmann R; (2005). Crit. Rev Oncol Hematol. 54(1):11-29). In general, the experimental evidences indicate that the pharmacokinetic properties of the ligand improve by decreasing its size (Reilly R. M., Sandhu J., Alvarez-Diez T. M., et al. (1995). Clin. Pharmacokinet. 28: 126142). Short- and medium-size peptides (typically 1 to 3 kDa) can overcome at least in part the complications faced with antibody-mediated anticancer therapies (Ladner R. C., Sato A. K., Gorzelany J., de Souza M. (2004). Drug Discov. Today 9: 525529). Particularly, peptides can display a better tumor penetration, lower unspecific uptake and elicit a lower immune response. Therefore, the peptides of the present invention are designed for optimized interaction with their receptor and significantly to guarantee an efficient biodistribution.

Usually, short- and medium-sized peptides up to 20-25 residues-long are poorly immunogenic, not the case for heterologous proteins and especially for microorganism-derived antigens as p25. The use of such proteins as therapeutic agents can generate an immune response in patients, followed by the induction of antibodies which could neutralize the therapeutic effect of the protein. This effect is particularly relevant for treating chronic illnesses that require the repeated use of therapeutic agents. On the other hand, if the microorganism is a pathogen for humans, it is plausible that a fraction of the population had developed neutralizing antibodies, which, pre-existing to treatment, could increase the therapeutic doses required. In this regard, since a significant part of the molecular surface of the Gly255-Ser274 segment is compromised within the interface between the N- and C-terminal domains of the p50 protein, and therefore cryptic in the native structure of the protein. Consequently, the resulting N06P87 peptide is potentially poorly immunogenic, that is, that the anti-p50 protein antibodies are inefficient at recognizing (neutralizing) the N06P87 peptide. Therefore, and regarding the antigenic/immunogenic potential of the therapeutic molecule, is more favorable to use peptides instead of complete proteins, especially when the peptides are able to promote a biological effect similar to that of the natural protein.

An essential aspect for designing potent anticancer agents in the present invention comprises the design of cyclic peptides, that is, they have amino acids coupled by covalent bonds involving chemical groups located in the side chains and/or groups at the N- and C-termini. Therefore, the peptides designed herein are structurally constrained by means of cyclization, which significantly reduces the structural flexibility of these molecules. Commonly, the use of peptides as therapeutic agents imposes some disadvantages. That is the case for the intrinsic flexibility of peptides, especially the short- and medium-sized ones which are far more flexible than folded proteins, and hence, their process for binding to proteins or other receptor macromolecules involves a significant loss of conformational entropy. This fact contributes to these molecules having as a rule a lower binding affinity than that of the protein-protein interaction. The lower affinity exhibited by peptides (and consequently, lower potency) could be also associated to the fact that the protein-receptor contact surface is smaller compared to the protein-receptor interfaces, particularly when peptides comprise a fragment of the native protein. For these reasons, a redesign and chemical modification of peptides are required to increase their affinity for receptor binding (and consequently, potency).

It was previously identified a polypeptide derived from an infection-mediated tumor regression model which was denominated p25, which showed antiangiogenic and direct effect on tumor cells (International Patent Application No. WO 2006/005268). In the present invention, a platform was developed based on peptides mimicking the active motif of the p25 polypeptide, and showing several improvements compared to the molecule of origin. The native polypeptide, bacterial in origin, can only be applied a limited number of times to treat cancer, due to the potential induction of immune responses which could neutralize its activity, hampering the prolonged treatment required in chronic diseases as cancer. That is the reason why in the present invention, the field of research was focused on generating molecules derived from infection-mediated tumor regression and useful for cancer therapy, by identifying the minimal functionally active unit in the p25 polypeptide resembling its anticancer activity, but unable to induce the negative immune response during prolonged administration for therapy of oncological or unwanted cellular proliferation pathologies.

A significant contribution of the present invention is the feasibility for developing peptide molecules of up to 25 amino acids, which structurally mimic the minimal functionally active unit of antitumor proteins derived from infection-mediated tumor regression. Surprisingly, these small molecules do not exert their activities against the tumor by immune-mediated mechanisms, as it was previously considered had to be as paradigm for the infection-mediated tumor regression (Paglia P, y Guzman C A. Cancer Immunol. Immunother. 1998. 46:88-92). Moreover, another novel aspect of the present invention involves that those active regions are not located on the exposed surface of bacterial proteins, but become superficial once the protein is enzymatically digested. This process can occur in the metalloproteinase-rich tumor environment, originating a strong cytotoxic effect against tumor cells and the tumor-associated angiogenesis. This could also contribute to the potent antitumor activity previously attributed to infection-mediated tumor regression, a field of research expecting for molecules useful for cancer therapy and able to become novel biotechnological products in oncological therapeutics for over a century. In the present document, this hypothesis is demonstrated as valid, since the peptides of the present invention showed to have antitumor efficacy in vitro and in vivo, in prolonged treatments, with no evidences on the presence of neutralizing antibodies which could limit their continuous administration. The technology used to obtain them is scalable. Among the advantages of these peptides are:

Wide spectra of action on tumor cells from different histological origins.

Direct action on tumor angiogenesis and direct action against tumor cells.

A p53-independent mechanism of action.

Cytotoxic effect on cells isolated from human metastasis and consequent antimetastatic effect.

Induce apoptosis on tumor cells and are specific for cells activated to proliferate.

Antitumoral effect either by systemic or intratumoral routes. Reduce the growth rate in xenografted tumors and prolong survival of tumor-carrying animals.

Complete tumor regression in a set of tumors.

Lack of toxicity during repeated injection in animals for a prolonged period.

Present a distribution volume higher than that of the molecule of origin.

The biodistribution profile supports treatment of malignant tumors of different pathologies.

Economically affordable production technologies.

More feasible and faster pharmaceutical development than that of molecules obtained by recombinant techniques.

The subjects of the present invention are cyclic peptides with antineoplastic and antiangiogenic activities, wherein said cyclic polypeptides are characterized by an amino acid sequence comprising:

a) A segment with the amino acid sequence:

$$X^1\text{-Asn-Thr-}X^2\text{-Arg-Asp-Phe-}X^3\text{-}X^4$$

Wherein, $X^1$ is an amino acid selected from the group comprising Ser, Cys, Lys, Asp, Glu and a non-natural amino acid which side chain comprises the sulfhydryl functional group, the amino group or a carboxyl group; or a sequence selected from the group comprising a tetrapeptide, a pentapeptide and a hexapeptide.

$X^2$ is the amino acid Gly or D-Ala $X^3$ is an amino acid selected from the group comprising Leu, Cys, Lys, Asp, Glu and a non-natural amino acid which side chain comprises the functional group sulfhydryl, the amino group or the carboxyl group $X^4$ is an optional amino acid which can be selected from the group comprising Ser, Cys, Lys, Asp, Glu and a non-natural amino acid which side chain comprises the functional group sulfhydryl, the amino group or the carboxyl group;

b) A N-terminal segment, optional and prior to the segment described in a), with the amino acid sequence:

$$X^{-5}\text{-Asp-Thr-Val-}X^{-4}\text{-}X^{-3}\text{-}X^{-2}\text{-}X^{-1}$$

Wherein, $X^{-1}$ is an amino acid selected from the group comprising Asn, D-Asp, D-Glu, D-Gln and D-Ala, and linked by a peptide bond to the $X^1$ residue described in a), and the said peptide bond comprises the carbonyl group on the main chain of the $X^1$ residue and the amino group on the main chain of the $X^1$ residue of the segment described in a);

$X^{-2}$ is an amino acid selected from the group comprising Phe, Cys, Lys, Asp, Glu and a non-natural amino acid which side chain comprises the functional group sulfhydryl, the amino group or the carboxyl group $X^{-3}$ is an amino acid selected from the group comprising Gly and D-Ala $X^{-4}$ is an amino acid selected from the group comprising Tyr, Cys, Lys, Asp, Glu and a non-natural amino acid which side chain comprises the functional group sulfhydryl, the amino group or the carboxyl group $X^{-5}$ is an amino acid selected from the group comprising Gly and D-Ala c) A C-terminal segment optional and posterior to the segment described in a) which amino acid sequence is selected from the group comprising Thr-$X^{+1}X^{+2}$, Thr-$X^{+1}$-$X^{+2}$-$X^{+3}$ and Thr-$X^{+1}$-$X^{+2}$-$X^{+3}$-$X^{+4}$ Where, The N-terminal Thr residue in the said C-terminal segment is linked to the segment described in a) by a peptide bond which comprises the amino group on the main chain of the said N-terminal Thr residue and the carbonyl group on the main chain of the $X^4$ residue of the segment described in a)

$X^{+1}$ is an amino acid selected from the group comprising Thr, Gly and Ala $X^{+2}$ is an amino acid selected from the group comprising Ser, Asn, Cys, Lys, Asp, Glu and a non-natural amino acid comprising the side chain the functional group sulfhydryl, the amino group or the carboxyl group $X^{+3}$ is an amino acid selected from the group comprising Cys, Gln, Arg, Asn, Lys, Asp, Glu and a non-natural amino acid comprising at the side chain the functional group sulfhydryl, the amino group or a carboxyl group $X^{+4}$ is an amino acid selected from the group comprising Gln, Arg, Asn and Lys d) At least a covalent bond selected from the group comprising a peptide bond formed by the amino and carbonyl groups of the N- and C-termini of the peptide that is present if the $X^1$ sequence of the segment described in a) is the sequence of a tetrapeptide, a pentapeptide or an hexapeptide; a covalent disulfide bridge comprising the sulfhydryl groups in the side chain of residues $X^1$ and $X^4$, or $X^{-4}$ and $X^3$, or $X^{-2}$ and $X^{+2}$, or $X^{-2}$ and $X^{+3}$ if said $X^1$ and $X^4$, or $X^{-4}$ and $X^3$, or $X^{-2}$ and $X^{+2}$, or $X^{-2}$ and $X^{+3}$ are cysteines or a non-natural amino acid which side chain comprises the sulfhydryl group; an amide bond comprising a carbonyl group and an amino group on the side chains of residues $X^1$ and $X^4$, or $X^{-4}$ and $X^3$, or $X^{-2}$ and $X^{+2}$, or $X^{-2}$ and $X^{+3}$ if said $X^1$ and $X^4$, or $X^{-4}$ and $X^3$, or $X^{-2}$ and $X^{+2}$, or $X^{-2}$ and $X^{+3}$ are Lys (or an non-natural amino acid which side chain comprises an amino group) and Glu (or Asp or a non-natural amino acid which side chain comprises a carbonyl group), or said residues are respectively Glu (or Asp or a non-natural amino acid which side chain comprises a carbonyl group) and Lys (or a non-natural amino acid which side chain comprises an amino group); and an amide bond comprising the carbonyl terminal group of the peptide and an amino group on the side chain of the residue $X^{-2}$ and said amide bond is present if the $X^{+2}$ is: the residue at the carboxyl terminus of the peptide, the Asn amino acid and $X^{-2}$ is the amino acid Lys or a non-natural amino acid which side chain comprises an amino group In a preferred embodiment of the present invention, cyclic peptides comprise a peptide bond between the amino and carbonyl groups of the N- and C-termini of the peptide and the $X^1$ sequence of said peptides is a tetrapeptide amino acid sequence, preferentially the sequence being selected from the group comprising (D-Ser)-Pro-Thr-Pro, (D-Ala)-Pro-Thr-Pro and Gly-Pro-Thr-Pro.

In another embodiment of the invention, said cyclic peptides comprise a peptide bond between the amino and carbonyl groups on the N- and C-terminal residues of the peptide and the $X^1$ sequence of said peptides is a pentapeptide amino acid sequence, preferentially the sequence being selected from the group comprising Arg-Arg-Pro-Asn-Ser, Arg-Arg-Pro-(D-Ala)-Ser, Lys-Lys-Pro-Asn-Ser and Lys-Lys-Pro-(D-Ala)-Ser.

In another embodiment of the invention, said cyclic peptides comprise a peptide bond between the amino and carbonyl groups on the N- and C-termini of the peptide and the $X^1$ sequence of said peptides has a hexapeptide amino acid sequence, preferentially the sequence being selected from the group comprising Thr-Pro-(D-Ala)-Gln-Asn-Ser, Arg-Pro-(D-Ala)-Gln-Asn-Ser, Thr-Pro-(D-Ala)-($_{Bm}$Gln)-($_{Nm}$Asn)-Ser and Arg-Pro-(D-Ala)-($_{Bm}$Gln)-($_{Nm}$Asn)-Ser, wherein $_{Bm}$Gln is the amino acid L-b-methylglutamine and $^{Nm}$Asn is the amino acid L-N-methyl asparagines.

In the invention the cyclic peptides could have the N-terminus covalently linked to the acetyl group, the pyroglutamic amino acid, to a lipid or a polymer, preferentially polyethylene glycol, and the bond could be established directly or through an spacer group, preferentially the amino acid Gly. Moreover, the cyclic peptides of the invention could have the C-terminus in the amide form, or covalently linked to a lipid or a polymer, preferentially polyethylene glycol and the bond being established directly or through a spacer, preferentially the amino acid Gly.

In another embodiment of the invention, cyclic peptides can comprise a covalent bond between the peptide and a lipid or any polymer, preferentially polyethylene glycol, and the said bond can comprise the sulfhydryl group, the amino group or the carboxyl group on the side chain of the residue $X^1$, $X^3$, $X^4$, $X^{-2}$, $X^{-4}$, $X^{+2}$ or $X^{+3}$, and the said $X^1$, $X^3$, $X^4$, $X^{-2}$, $X^{-4}$, $X^{+2}$ or $X^{+3}$ residue is the amino acid Cys, Lys, Asp, Glu or a non-natural amino acid which side chain comprises the functional group sulfhydryl, the amino group or the carboxyl group.

In another embodiment of the invention, cyclic peptides can be characterized by the $X^1$, $X^3$, $X^4$, $X^{-2}$, $X^{-4}$, $X^{+2}$ or $X^{+3}$ residues being selected from the group comprising the amino acid cysteine, the (2R)-2-amino-3-sulfanylbutanoic acid, the (2R)-2-amino-3-methyl-3-sulfanylbutanoic acid, the (2S)-2-amino-4-sulfanylbutanoic acid, the 2-amino-5-sulfanyl-pentanoic acid, the 2-amino-3-sulfanyl-pentanoic acid, the 2-amino-4-methyl-3-sulfanylpentanoic acid, the 2-amino-3-methyl-4-sulfanylpentanoic acid, the 2-amino-3,4-dimethyl-3-sulfanyl-pentanoic acid, the 2-amino-3-ethyl-3-sulfanyl-pentanoic acid, the (2R)-2-amino-3-methyl-3-sulfanylpentanoic acid, the (4S)-4-amino-2-methyl-5-sulfanylpentanoic acid, the (4R)-4-amino-2-methyl-5-sulfanylpentanoic acid, the (4R)-4-amino-5-sulfanylpentanoic acid, and the (4S)-4-amino-5-sulfanylpentanoic acid. In another embodiment of the invention, cyclic peptides can be characterized by the $X^1$, $X^3$, $X^4$, $X^{-2}$, $X^{-4}$, $X^{+2}$ or $X^{+3}$ residues being selected from the group comprising the amino acid Lys, the 2-[bis(3-aminopropyl)amino]acetic acid, the (2S)-2,5-diaminopentanoic acid, the 2,2-diaminoacetic acid, the (3S)-3,4-diaminobutanoic acid, the (2R)-2,4-diaminobutanoic acid, the (2S)-2,4-diaminobutanoic acid, (2S)-2,3-diaminopropanoic acid, the (2R)-2,3-diaminopropanoic acid, the 2-[(2-aminoethyl)amino]acetic acid, the 2-[(3-aminopropyl)amino]acetic acid, the 2-[(4-aminobutyl)amino]acetic acid, the (4S)-4,8-diaminooctanoic acid, the (2S)-2-amino-3-(4-aminophenyl)propanoic acid, the (2S)-2-amino-3-[4-(2-aminoetoxi)phenyl]propanoic acid, the 2-(piperidin-4-ylamino)acetic acid, the (2S)-2-amino-4-[(5R)-2,2-dimethyl-1,3-oxazolidin-5-yl]butanoic acid, the (2S)-2-amino-6-(methylamino)hexanoic acid, the (2R,4R)-4-aminopirrolidine-2-carboxylic acid or the (2R,4S)-4-aminopirrolidine-2-carboxylic acid, the 2-(4-aminopiperidin-4-yl)acetic acid, the 4-aminopiperidine-4-carboxylic acid, the (2S,4R)-4-aminopirrolidine-2-carboxylic acid and the imidazolidine-2-carboxylic acid.

In another preferred embodiment of the invention, cyclic peptides can be characterized by the $X^1$, $X^3$, $X^4$, $X^{-2}$, $X^{-4}$, $X^{+2}$ or $X^{+3}$ residues being selected from the group comprising the amino acid Glu, Asp, the 3-[(carboxymethyl)amino]propanoic acid, the 2-[(carboxymethyl)amino]acetic acid, the 3-[(2-carboxyethyl)amino]propanoic acid, the (3R)-3-aminohexanedioic acid, the 4-aminoheptanedioic acid, the 4-aminopiperidine-1,4-dicarboxylic acid, the (2S,4S)-4-aminopirrolidine-2-carboxylic acid, the 2-[(carboxymethyl)amino]acetic acid, the (2S)-2-amino-6-[(carboxymethyl)amino]hexanoic acid, the 3-[(2-carboxyethyl)amino]propanoic acid, the (2S)-2-aminoheptanedioic acid, the (2S)-2-aminooctanedioic acid, the (2R)-2-amino-3-[(2-carboxyethyl)sulfanyl]propanoic acid, the (2R)-2-amino-3-[(carboxymethyl)sulfanyl]propanoic acid, the 4-{[(2R)-2-amino-2-carboxyethyl]sulfanyl}butanoic acid and the (2S)-2-amino-3-[4-(carboxymethoxi)phenyl]propanoic acid.

In a particular embodiment of the invention, the cyclic peptides with antitumoral and antiangiogenic effect have an amino acid sequence selected from sequences SEQ ID 1-76.

It is a subject of the present invention the use of the said cyclic peptides to prepare a medicine for cancer therapy or to treat undesired cellular proliferation-related disorders, or an antiangiogenic medicine.

Another embodiment of the invention comprises a method to treat cancer, undesired cellular proliferation-related disorders and undesired angiogenesis, wherein said method comprises the administration of a pharmaceutical composition comprising an effective amount of at least one of the cyclic peptides of the invention to an individual who need it. Pharmaceutical compositions comprising at least one of the peptides of the present invention and excipients or pharmaceutically suitable vehicles are also subject of the present invention.

The invention also provides compounds for cancer diagnosis comprising at least one of the peptides of the invention and an agent for imaging, wherein said agent for imaging is selected from the group comprising a fluorescent group, a non-fluorescent group, a semiconductor fluorescent particle, a paramagnetic or superparamagnetic agent, and a radioisotope.

Another aspect of the present invention comprises a pharmaceutical combination comprising at least one of the peptides of the invention together with at least one agent for treatment such as anticancer drugs and hormones. In an embodiment of the invention, in the said combination the peptide is conjugated directly to the treatment agent by covalent bonds. In another cases, the peptide is conjugated to the treatment agent by a coupling element.

The invention also comprises the pharmaceutical combinations comprising at least one of the peptides of the invention combined with prodigiosins or their derivatives. The elements forming such combinations can be administered to the individuals who require them, within the course of a medical treatment, either sequentially or simultaneously.

A large number of medicines must be administered by parenteral route, for example: intravenous injection, intramuscular or subcutaneous route, to achieve the intended therapeutic efficacy. For some therapeutics, the use of controlled release vehicles could increase the efficacy of the drug and the satisfaction degree of the patient. The molecular self-assembly has been recently explored to engineer materials for encapsulation and controlled release of therapeutics. There is a great progress in designing self-assembly material platforms based on peptides and polymers (Monica C. Branco a,b, Joel P. Schneider. Acta Biomaterialia 5 (2009) 817-831). Some of the peptides of the present invention, such as the J08P48 bear amphipathic properties allowing it to self-assemble, and, therefore, to be part of controlled release systems for therapeutic molecules or in the field of nanotechnology. Therefore, are subject of the present invention the novel encapsulated formulations in the form of liposomes or microspheres for controlled release of these peptides as medicines for combined therapies against cancer. And also the nanoparticulated complexes with controlled targeting systems for the diagnosis-therapeutic sites of interest or exerting by themselves these activities in a specific manner.

DETAILED DESCRIPTION OF THE EMBODIMENT/EXAMPLES

Figure 1:
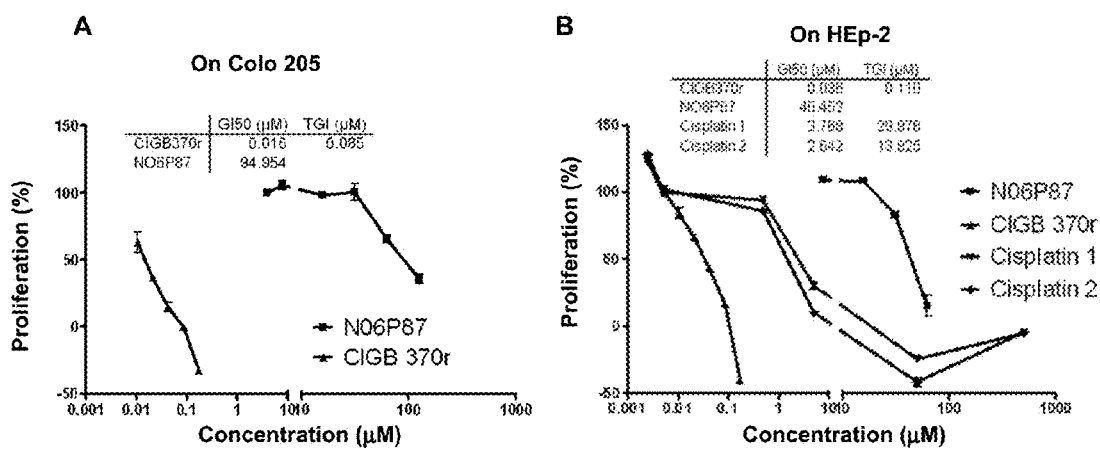
FIG. 1. Cytotoxic activity of the N06P87 peptide on tumor cells from different histological origins. A: Colo 205 cells; B: HEp-2 cells. The CIGB370r polypeptide and the Cisplatin were used as positive controls of antitumor agents.

Examples and data show several aspects and properties related to obtaining the cyclic peptides, starting from a library of linear synthetic peptides and the tertiary structure of a polypeptide corresponding to the C-terminus of the PRZN_SERMA Serralysin (Braunagel S C, and Benedik M J (1990). Mol. Gen. Genet. 222:446-451), denominated p25, of proven pharmaceutical potentialities (Abrahantes-Pérez M C et al., "Pharmaceutical composition containing polypeptide fragments of serralysins". International Patent Application No. WO 2006/005268).

Examples shown in the following relate the compounds and/or the methods of the present invention, including the use of molecules derived from these peptides, optimized and/or derivatives. Compared to the previous state of the art, the compounds and methods shown herein provide surprising and challenging the expectations. The usefulness of the invention is illustrated by using these compounds in the pharmaceutical field. Said compounds bear advantages compared to other compounds known by specialists skilled in this field of technique.

Example 1

Design and Synthesis of a Library of Linear Peptides Derived from the p25 Polypeptide Linear peptides of 20 amino acids (aa.) overlapped in 10 were designed, aimed at identifying the minimal functionally-active unit of the p25 polypeptide (Abrahantes-Pérez MC y col., "Pharmaceutical composition containing polypeptide fragments of serralysins". International Patent Application No. WO 2006/005268) and to generate new molecules from that region with improved pharmacological and pharmacodynamic properties for cancer treatment. That would imply the identification of active regions comprised in a primary sequence of 10 to 20 aa. Table 1 show the primary sequence of each peptide, its generation code and its molecular mass once synthesized and purified. Molecular mass of final peptide preparations were verified by mass spectrometry.

TABLE 1

Design and synthesis of a library of linear peptides starting from the primary sequence of the p25 polypeptide

| Peptide | Amino acid sequence | Code | Molecular mass (Da) |
|---|---|---|---|
| MJ01 | SYWSETNTGGDNGGHYAAAP-amide | D06P91 | 2052.85 |
| MJ02 | DNGGHYAAAPLLDDIAAIQH- amide | E07P01 | 2060.00 |

TABLE 1-continued

Design and synthesis of a library of linear peptides starting from the primary sequence of the p25 polypeptide

| Peptide | Amino acid sequence | Code | Molecular mass (Da) |
|---|---|---|---|
| MJ03 | LLDDIAAIQHLYGANPSTRT- amide | E07P05 | 2167.10 |
| MJ04 | LYGANPSTRTGDTVYGFNSN- amide | E07P06 | 2131.98 |
| MJ05 | GDTVYGFNSNTGRDFLSTTS- amide | J07P73/N06P87 | 2137.10 |
| MJ06 | TGRDFLSTTSNSQKVIFAAW- amide | F07P16 | 2227014 |
| MJ07 | NSQKVIFAAWDAGGNDTFDF- amide | M07P38 | 2192.50 |
| MJ08 | DAGGNDTFDFSGYTANQRIN- amide | M07P39 | 2160.97 |
| MJ09 | SGYTANQRINLNEKSFSDVG- amide | A07P42 | 2198.08 |
| MJ10 | LNEKSFSDVGGLKGNVSIAA- amide | A07P47 | 2004.06 |
| MJ11 | GLKGNVSIAAGVTIENAIGG- amide | A07P44 | 1839.01 |
| MJ12 | GVTIENAIGGSGNDVIVGNA- amide | A07P45 | 1854.96 |
| MJ13 | SGNDVIVGNAANNVLKGGAG- amide | Y07P48 | 1824.92 |
| MJ14 | ANNVLKGGAGNDVLFGGGGA- amide | A07P43 | 1785.95 |
| MJ15 | NDVLFGGGGADELWGGAGKD- amide | A07P46 | 1932.87 |
| MJ16 | DELWGGAGKDIFVFSAASDS- amide | O07P102 | 2070.08 |
| MJ17 | IFVFSAASDSAPGASDWIRD- amide | O07P103 | 2110.13 |
| MJ18 | APGASDWIRDFQKGIDKIDL- amide | O07P104 | 2243019 |
| MJ19 | FQKGIDKIDLSFFNKEANSS- amide | O07P105 | 2286.19 |
| MJ20 | SFFNKEANSSDFIHFVDHFS- amide | O07P106 | 2373.20 |
| MJ21 | DFIHFVDHFSGTAGEALLSY- amide | O07P107 | 2224.07 |
| MJ22 | GTAGEALLSYNASSNVTDLS- amide | O07P108 | 1967.99 |
| MJ23 | NASSNVTDLSVNIGGHQAPD- amide | E02P04 | 1993.95 |
| MJ24 | VNIGGHQAPDFLVKIVGQVD- amide | E07P02 | 2104.14 |
| MJ25 | FLVKIVGQVDVATDFIV- amide | E07P03 | 1861.11 |
| MJ26 | DVATDFIV- amide | U07P78 | 877.46 |

Peptides were synthesized in solid phase on the Fmoc-AM-MBHA resin, by using the Fmoc/tBu strategy (Barany, G. and Merrifield, R. B. J Am Chem. Soc. 99 (1977) 7363-7365). Amino acids were coupled by the method of DIC/HOBt-mediated activation and completeness of the coupling reaction was verified by the ninhydrin assay (Kaiser, E., Colescott, R. L., Bossinger, C. D., Cook, P. I. Anal Biochem. 34 (1970) 595-598). Peptides were detached from the resin with a TFA/EDT/H$_2$O/TIS (94%/2.5%/2.5%/1%) solution; further ether precipitated and lyophilized for 72 h. Cyclization was achieved by forming a disulfide bridge through oxidation with dimethyl sulfoxide (DMSO) (Andreu, D., Albericio, F., Solé, N. A., Munson, M. C., Ferrer, M. and Barany, G., Pennington, M. W. and Dunn, B. M. (Eds), Peptide Synthesis Protocols, Methods in Molecular Biology, Totowa, N.J., 1994, pp. 91-169) and the peptides were further purified by RP-HPLC. Fractions collected were analyzed independently by analytic RP-HPLC and the final preparation for each peptide was formed by pooling all the respective fractions showing purity above 99%.

Example 2

Selection of Primary Sequences from the Library of Synthetic Peptides Derived from the p25 Polypeptide, Based on their Cytotoxic Activity in Vitro on Tumor Cells The cytotoxic activity of the synthetic peptide library derived from the p25 polypeptide was determined on tumor cells by the sulforhodamine B (SRB) method (Skehan P, Storeng R, Scudiero D, et al., (1990) J. Natl. Cancer Inst. 82: 1107-1112; Monks A, Scudiero D, Skehan P, et al., (1991). J Natl Cancer Inst. 83:757-66; Tesei A, Ulivi P, Fabbri F, et al., (2005). J Transl Med. 3:7). Negative control cells were cultured on a volume of vehicle equal to that of the experimental samples. An "x-y" curve (dose-response) was established with the percent of surviving cells, compared in respect to the negative control cells, and the following parameters were estimated: 50% growth inhibition (GI50); Total growth inhibition (TGI); and the lethal concentration 50 (LC50), that is the concentration causing the 50% of cell death (Boyd M R, Paull K D, and Rubinstein L R (1992) "Data display and analysis strategies for the NCI Disease Oriented In-Vitro Antitumor Drug Screen, in Cytotoxic Anticancer Drugs: Models and Concept for Drug Discovery and Development" (Baleriote F A, Corbett T H and Baker L H eds) pp 11-34, Kluwer Academia Publishers, Boston).

Were considered as cytotoxic peptides all those peptides being able of inhibiting 50% of the cellular proliferation, in a dose-dependent manner, and showing GI50 values below 100 µM, at least in one of the cell lines studied. The human tumor cell lines used were: HEp-2 (larynx carcinoma), A549 (lung epithelial adenocarcinoma), M14 (melanoma), Colo 205 (colon adenocarcinoma), Ls174T (colon adenocarcinoma), LnCAP (prostate carcinoma), PC-3 (prostate carcinoma) and H 125 (non-small cell lung adenocarcinoma). Results from this peptide screening are shown in Table 2. Represented are primary sequences for the designed peptides, the code used for its generation and their respective cytotoxic capacity on human tumor cells.

TABLE 2

Peptide screening based on the cytotoxic activity showed on human tumor cells in vitro by the SRB method

| Amino acid sequence | Code | Cytotoxic activity in vitro |
|---|---|---|
| SYWSETNTGGDNGGHYAAAP-amide | D06P91 | − |
| DNGGHYAAAPLLDDIAAIQH-amide | E07P01 | − |
| LLDDIAAIQHLYGANPSTRT-amide | E07P05 | − |
| LYGANPSTRTGDTVYGFNSN-amide | E07P06 | − |
| GDTVYGFNSNTGRDFLSTTS-amide | J07P73/ N06P87* | +/+ |
| TGRDFLSTTSNSQKVIFAAW-amide | F07P16 | − |
| NSQKVIFAAWDAGGNDTFDF-amide | M07P38 | − |
| DAGGNDTFDFSGYTANQRIN-amide | M07P39 | − |
| SGYTANQRINLNEKSFSDVG-amide | A07P42 | − |
| LNEKSFSDVGGLKGNVSIAA-amide | A07P47 | − |
| GLKGNVSIAAGVTIENAIGG-amide | A07P44 | − |
| GVTIENAIGGSGNDVIVGNA-amide | A07P45 | − |
| SGNDVIVGNAANNVLKGGAG-amide | Y07P48 | − |
| ANNVLKGGAGNDVLFGGGGA-amide | A07P43 | − |
| NDVLFGGGGADELWGGAGKD-amide | A07P46 | − |
| DELWGGAGKDIFVFSAASDS-amide | O07P102 | − |
| IFVFSAASDSAPGASDWIRD-amide | O07P103 | − |
| APGASDWIRDFQKGIDKIDL-amide | O07P104 | − |
| FQKGIDKIDLSFFNKEANSS-amide | O07P105 | − |

TABLE 2-continued

Peptide screening based on the cytotoxic activity showed on human tumor cells in vitro by the SRB method

| Amino acid sequence | Code | Cytotoxic activity in vitro |
|---|---|---|
| SFFNKEANSSDFIHFVDHFS-amide | O07P106 | − |
| DFIHFVDHFSGTAGEALLSY-amide | O07P107 | − |
| GTAGEALLSYNASSNVTDLS-amide | O07P108 | − |
| NASSNVTDLSVNIGGHQAPD-amide | E02P04 | + |
| VNIGGHQAPDFLVKIVGQVD-amide | E07P02 | − |
| FLVKIVGQVDVATDFIV-amide | E07P03 | − |
| DVATDFIV-amide | U07P78 | − |

Symbol + indicates the presence of cytotoxicity and symbol − indicates its absence, following criteria established in Example 2.
*This peptide was synthesized twice to guarantee the reproducibility of the results obtained.

The peptide GDTVYGFNSNTGRDFLSTTS-amide (Code N06P87/J07P73) was positive (+) for several tumor cell lines, while the peptide NASSNVTDLSVNIG-GHQAPD-amide (Code E02P04) only showed activity on the human melanoma M14 cell line. The rest of peptides were considered negative (−).

Figure 2:
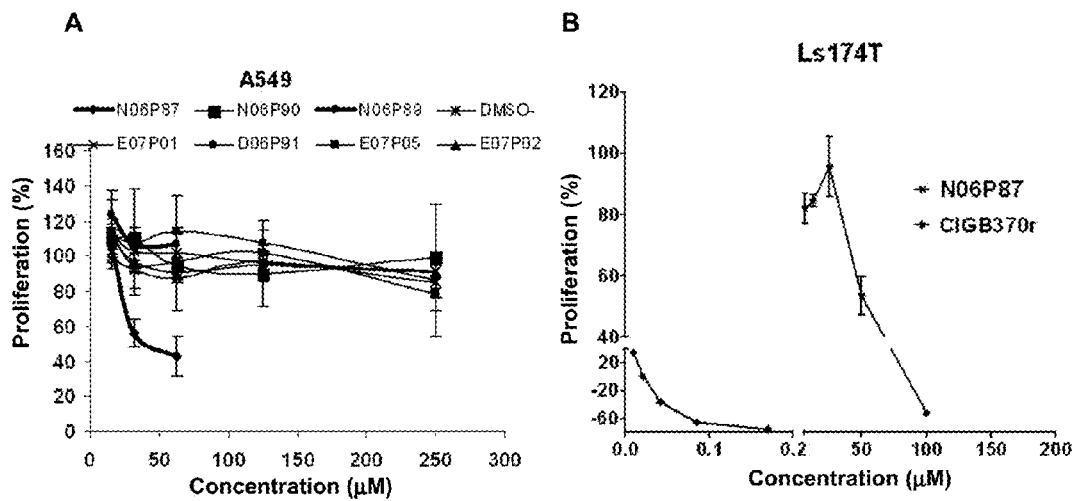
FIG. 2. Cytotoxic activity of the N06P87 on the non-small cells lung cancer cell line A549 (A) and on the colon cancer cell line (B). Other peptides of the library did not show activity when evaluating their effect on the A549 cell line proliferation.

FIGS. 1 and 2 represent the potentiality of the N06P87 to inhibit proliferation of human tumor cells of diverse histological origin, from the Colo 205, HEp-2, A549, and Ls174T cell lines. The GI50 was below 100 µM for all the cases. Two batches of Cisplatin were used as positive control in the case of the HEp-2 larynx carcinoma. This is a first-line product available in the market for larynx cancer treatment. In this assay its usefulness was demonstrated in this type of pathology and also the validity of the assay.

Figure 3:
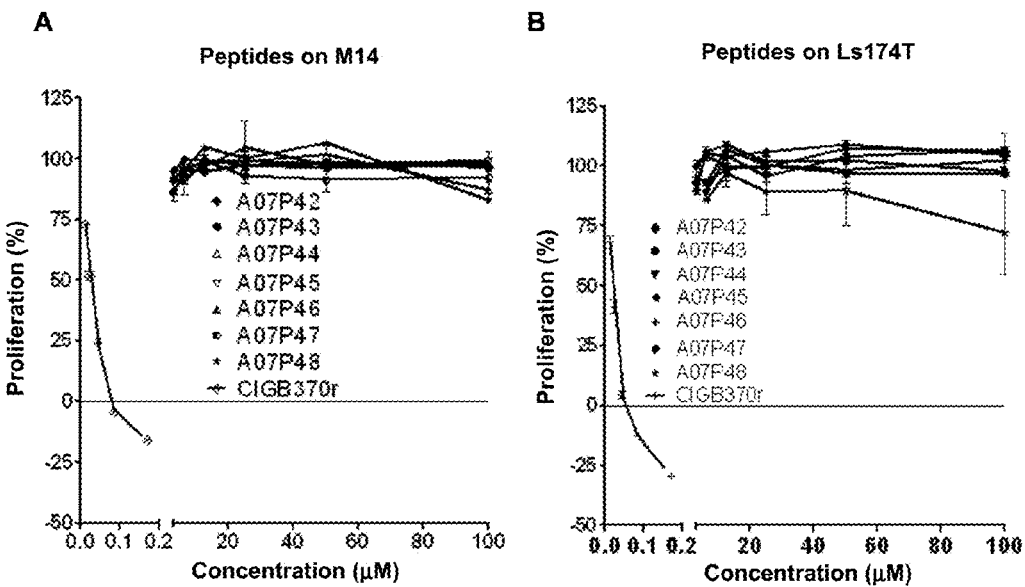
FIG. 3. Assays to evaluate the activity of several peptides from the library subject of study on the human tumor cell lines M14 (A) and Ls174T (B). The CIGB370r polypeptide was used as positive control in both assays.

Results from the evaluation of the effects for some peptides from the library in Table 1 on the human M14 and Ls174T tumor cell lines are shown in FIG. 3. This panel of peptides was unable to inhibit cellular proliferation on the assayed cell lines.

Figure 4:
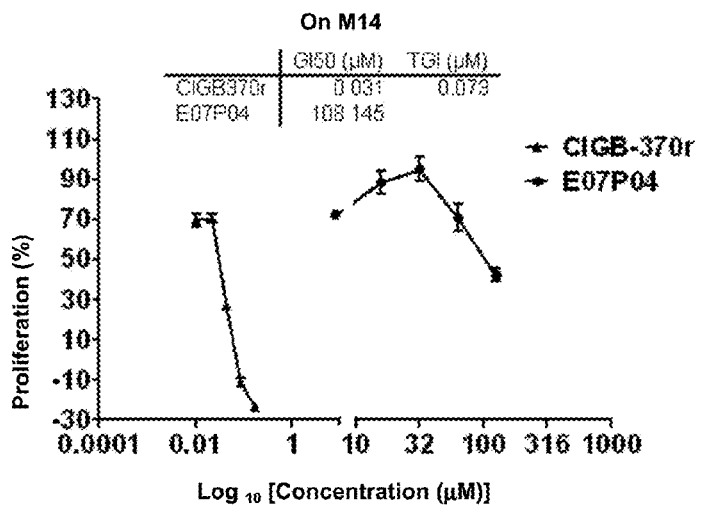
FIG. 4. Cytotoxic activity of the E07P04 peptide on the melanoma cell line M14. The CIGB370r polypeptide was used as positive control for the assay.

In addition to the N06P87 peptide spanning region, the 20 aa. region coded by the E07P04 peptide (Table 1) showed cytotoxic activity, but only on the M14 cell line and for a GI50 higher than 100 µM, as shown in FIG. 4.

Table 2 summarizes all the results from the peptide screening for cytotoxic acivity on tumor cells, evidencing that the GDTVYGFNSNTGRDFLSTTS-amide peptide comprising the Gly255-Ser274 region on the Serralysin PRZN_SERMA C-terminus domain and located at the N-terminus region of the p25 polypeptide is active on tumor cell lines of diverse histological origin, reproducing the wide spectrum of cytotoxic activity displayed by the original p25 molecule. All these suggested that the peptide identified as cytotoxic herein can be assumed as the minimal structurally-active sequence on the p25 polypeptide, to be further optimized for pharmacological applications against cancer.

Example 3

Impact of the N-Terminus Domain Removal on the Exposure in Solution of p50 Protein Residues It is well known that the C-terminus region of Serralysins (e.g., Serralysin PRZN_SERMA) is responsible for most of the cytotoxic activity on tumor cells, once cleaved the N-terminus from the protein by autocatalysis, chemical digestion with Cyanogen bromide, or by expressing the C-terminus in *Escherichia coli* (International Patent Application No. WO 2006/005268). That suggested that the minimal functionally-active unit in the C-terminus region of Serralysins was promoting their accessibility to tumor cells once separated from the protein N-terminus. Therefore, it was decided to identify the protein residues mediating its solvent accessibility surface after splitting the N- and C-termini of the native protein, also to corroborate if the Gly$_{255}$-Ser$_{274}$ (N06P87) peptide bear such residues. To test this hypothesis, accessibility calculations were made for the surfaces of the N- and C-termini of the major *Serratia* protease (Hamada K, Hata Y, Katsuya Y, Hiramatsu H, Fujiwara T, Katsube Y. (1996) *J. Biochem.* 119:844-851).

Figure 5:
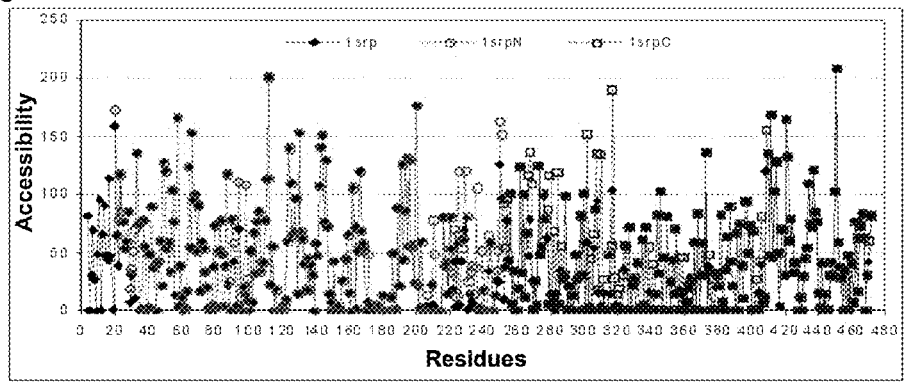
FIG. 5. Accessibility calculations of the surfaces of the N-terminal (1srpN) and C-terminal (1srpC) domains of the major *Serratia* protease, compared to the native protein (1srp).

The amino acid regions at the inner parts of the N- and C-termini domains becoming accessible once the proteolytic digestion of *Serratia* proteases produces both molecules were identified. The accessibility surface calculation for the residues was made with the DSSP software (Kabsch W, Sander C. 1983. Biopolymers 22:2577-2637). Accessibility values for the residues were expressed in Angstroms ($Å^2$). As shown in FIG. 5, the main differences in the accessibility values corresponded to aminoacids located at the C-terminus region in the N-terminus proteolytic domain (Gln210, Phe211, Asn226, His229, Leu236, Ile239, Ser251) and at the N-terminal region in the C-terminus non-proteolytic domain (Thr252, Phe269, Ile280, Trp284, Arg302, and Phe310) of the major *Serratia* protease. Residues showing the most significant changes in accessibility values are shown in Table 3.

TABLE 3

Amino acid (aa.) residues showing the most signifcant changes in accesibility values

| aa. | Residue | 1srp | 1srpN | Order |
|---|---|---|---|---|
| N | 20 | 159 | 173 | 51 |
| I | 22 | 39 | 80 | 21 |
| I | 24 | 76 | 85 | 60 |
| S | 29 | 7 | 20 | 53 |
| S | 31 | 32 | 51 | 46 |
| N | 32 | 11 | 70 | 13 |
| L | 91 | 43 | 58 | 50 |
| Q | 94 | 71 | 111 | 25 |
| D | 98 | 14 | 109 | 5 |
| V | 99 | 8 | 28 | 45 |
| Q | 210 | 6 | 78 | 9 |
| F | 211 | 3 | 49 | 19 |
| T | 222 | 19 | 33 | 52 |
| G | 223 | 43 | 70 | 37 |
| G | 224 | 4 | 13 | 61 |
| D | 225 | 59 | 121 | 11 |
| N | 226 | 5 | 66 | 12 |
| G | 227 | 43 | 54 | 57 |
| H | 229 | 70 | 121 | 17 |
| A | 231 | 2 | 26 | 41 |
| A | 232 | 15 | 34 | 47 |
| A | 233 | 9 | 39 | 33 |
| P | 234 | 6 | 15 | 62 |
| L | 235 | 5 | 37 | 30 |
| L | 236 | 0 | 106 | 2 |
| I | 239 | 3 | 52 | 18 |
| Q | 243 | 34 | 65 | 31 |
| A | 248 | 27 | 35 | 64 |
| N | 249 | 25 | 53 | 35 |
| L | 250 | 126 | 163 | 28 |
| S | 251 | 97 | 152 | 16 |
| R | 267 | 47 | 117 | 10 |
| D | 268 | 79 | 137 | 14 |
| F | 269 | 26 | 110 | 8 |
| K | 278 | 63 | 87 | 42 |
| I | 280 | 15 | 117 | 4 |
| F | 281 | 3 | 15 | 55 |

TABLE 3-continued

Amino acid (aa.) residues showing the most signifcant changes in accesibility values

| aa. | Residue | 1srp | 1srpN | Order |
|---|---|---|---|---|
| A | 282 | 11 | 68 | 15 |
| W | 284 | 15 | 119 | 3 |
| A | 286 | 35 | 56 | 43 |
| R | 302 | 59 | 152 | 6 |
| N | 304 | 4 | 45 | 22 |
| N | 306 | 54 | 66 | 56 |
| K | 308 | 94 | 135 | 23 |
| F | 310 | 4 | 134 | 1 |
| D | 312 | 16 | 27 | 58 |
| L | 316 | 15 | 57 | 20 |
| K | 317 | 104 | 190 | 7 |
| G | 318 | 2 | 29 | 38 |
| N | 319 | 5 | 14 | 63 |
| S | 321 | 3 | 19 | 49 |
| A | 323 | 1 | 31 | 34 |
| A | 324 | 36 | 57 | 44 |
| V | 339 | 17 | 55 | 27 |
| V | 341 | 0 | 40 | 26 |
| V | 357 | 18 | 46 | 36 |
| F | 359 | 15 | 46 | 32 |
| I | 375 | 38 | 49 | 59 |
| S | 379 | 20 | 33 | 54 |
| D | 403 | 0 | 27 | 39 |
| S | 405 | 16 | 43 | 40 |
| F | 406 | 40 | 81 | 24 |
| K | 409 | 120 | 155 | 29 |
| I | 470 | 42 | 60 | 48 |

Accessibility calculations of the surfaces of the N-terminus (1srpN) and C-terminus (1srpC) of the major protease of *Serratia*, compared to the native protein (1rp). Residues are ordered according to the value of the difference in exposure (Order column). The 64 residues showing the highest values for increased exposure are presented.

The residues pairs Asp98 and Arg267, and Asp225 and Lys317, establish two disulfide bridges between the N- and C-termini domains. Moreover, those residues show an average difference in accessibility values of 78.2 $Å^2$. The average difference in the accessibility values for the proteolytic N-terminus and the non-proteolytic C-terminus of the major *Serratia* protease were 5.1±15.4 $Å^2$ and 7.1±20.1 $Å^2$, respectively. Other relevant positions were: Ile22, Asn32, Gln94, and Arg171. So far, no biological activity has been attributed to these residues.

In contrast, neither the active site residues (His176, Glu177, and His180) located at α-helix E in the N-terminus proteolytic domain nor the Gly183 and His186 residues included in the zinc-binding motif HEXXHXXGXXH showed any changes in their respective accessibility values. These data are in agreement with the experimental results; efficiently demonstrating that the cytotoxic activity of the p50 protein (which belongs to the family of Serralysins) does not depend on its proteolytic activity, and is associated to its non-proteolytic C-terminus region, which increases its solvent accessibility once cleaved away from the proteolytic domain. On the other hand, the Gly255-Ser274 segment (peptide N06P87) bear three residues (Arg267, Asp268 y Phe269) of those showing the highest increase in exposure (Table 3), specifically among the highest 14 values, further supporting the apparent role of this segment as structurally functional unit within the p25 protein responsible for the antitumor activity.

Example 4

Modifications to the Gly255-Ser274 Segment of the N06P87 Peptide

Figure 6:
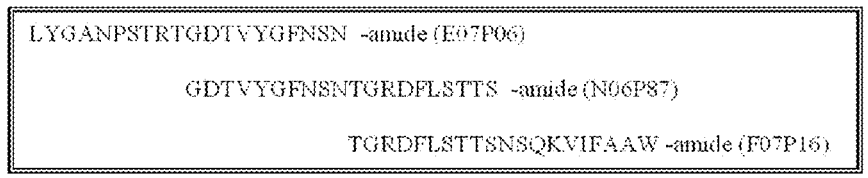
FIG. 6. Sequences flanking the 20-amino acids leader peptide (aa) N06P87.

The peptide library shown in Example 1 comprises 20 aa.-long segments overlapped in 10 aa, starting from the N-terminus of the p25 polypeptide. This design was established aimed at identifying a linear region of 10 aa. related to the cytotoxic activity subject of the screening. However, the overlapped 10 aa. comprised by the N06P87 showed no cytotoxic activity (Table 2) in another context (FIG. 6, peptides E07P06 and F07P16). This suggests that the 20 aa. comprising the Gly255-Ser274 region (peptide N06P87) are required for establishing the right exposure of the motif for interaction with tumor cells or proper positions for secondary interactions flanking the active site, increasing by this means their affinity and/or specificity to bind the potential receptor. Considering this criterion, peptides were designed and synthesized bearing modifications, to evaluate their possible influences on the cytotoxic activity vs. tumor cells and for partial characterization of the N06P87 peptide for further optimizations. Such modifications comprised the substitution of the amide group by a carboxyl group at the C-terminus of the N06P87 peptide, and cyclization of the N06P87 peptide by inserting one cysteine in both termini of the peptide. The peptides obtained and their molecular masses are shown in table 4.

TABLE 4

Modifications to the 20 aa. leader peptide N06P87

| Peptide | Amino acid sequence | Code | Molecular mass (Da) |
|---|---|---|---|
| MJ27 | GDTVYGFNSNTGRDFLSTTS-amide | N06P87 | 2136.94 |
| MJ28 | GDTVYGFNSNTGRDFLSTTS-OH | U07P79 | 2137.91 |
| MJ29 | cyclo [GDTVYGFNSNTGRDFLSTTS] | N06P89 | 2340.97 |

Figure 7:
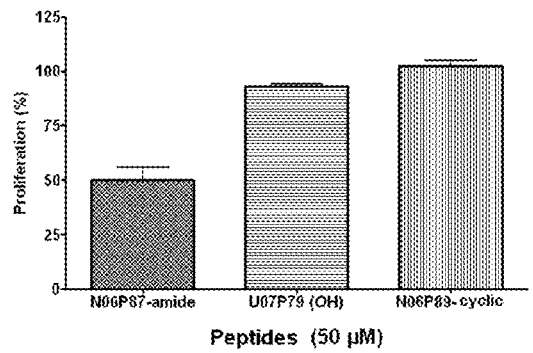
FIG. 7. Cytotoxic activity on human Melanoma cells. The leader peptide N06P87 was the only one capable to inhibit cellular proliferation at a 50 µM concentration.

The inability of peptide N06P89 (cyclized by two cysteines located at both N- and C-termini) to inhibit cellular proliferation in M14 human melanoma tumor cells is shown in FIG. 7. This suggests the need for further constrains to be added at other positions on the N06P87 peptide sequence, supporting the rationale of mimicking the tertiary structure this region has on the putative structure of the p25 polypeptide. At the same FIG. 7, it is also shown the need for blocking the C-terminus (for example, an amide group or other modification) to achieve the cytotoxic capacity expected for the peptide region of interest.

Example 5

Formulations of the Leader Peptide do not Increase its Cytotoxic Activity

A study was conducted to evaluate the influence of buffer conditions, pH and additives of several parenteral formulations containing the leader peptide on its cytotoxic activity in tumor cells. Among buffers evaluated were; glycine, phosphates, citrates, and others comprising a wide range of pH values, from acidic to highly basic. There were also evaluated several additives within the range of use for parenteral formulations, such as: glycine, sucrose, dextran, sodium glutamate, sorbitol, cyclodextrin, PEG, EDTA, non-ionic detergents and others. The N06P87 peptide formulated on these additives showed no increased on its cytotoxic activity in tumor cells from diverse histological origins.

Example 5

In Vivo Activity of the Linear Peptide N06P87

The Ls174T colon cancer tumor model in athymic mice was used to evaluate the potential effect of the linear Gly255-Ser274 segment (peptide N06P87), compared to the CIGB370r polypeptide, on human tumor models. Human tumor cells were administered by subcutaneous route, and the molecules of interest or the vehicle were administered by intratumor route (100 μL). After 13 days, when tumors were implanted and palpable, administration schedules started for the molecules of interest (FIG. 8A). The peptide N06P87 was administered in down-scaled doses: two administrations of 600 μM each every 48 h, followed by 4 administrations of 330 μM each every 48 h, and lastly 4 administrations of 90 μM each every 72 h. The CIGB370r peptide was administered weekly for 4 weeks.

Thirty-five days after treatment start, significant differences were detected in tumor volume ($p<0.001$) among the groups treated with the N06P87 and the vehicle (FIG. 8B). Moreover, there were highly significant differences ($p<0.0001$) between the groups treated with the CIGB370r and the one receiving vehicle, as detected by a one-tailed ANOVA with Bonferroni's post test. There were also highly significant differences between the groups receiving both molecules ($p<0.0001$).

Figure 8:
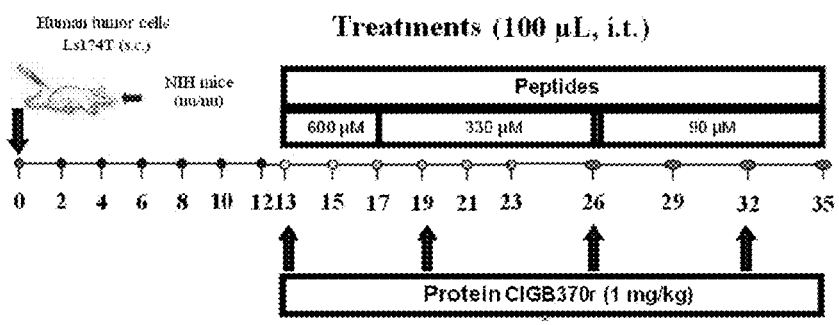
FIG. 8. Evaluation of the antitumoral capacity of the linear peptide N06P87, derived from the p25 polypeptide, compared to the molecule of origin. Administration schedule (A); Antitumor effect evaluated by measuring the tumor volume (B); and Antitumor effect evaluated through survival of inoculated mice (C). Model used: human colon cancer Ls174T cell line implanted in NIH athymic mice.
Figure 8:
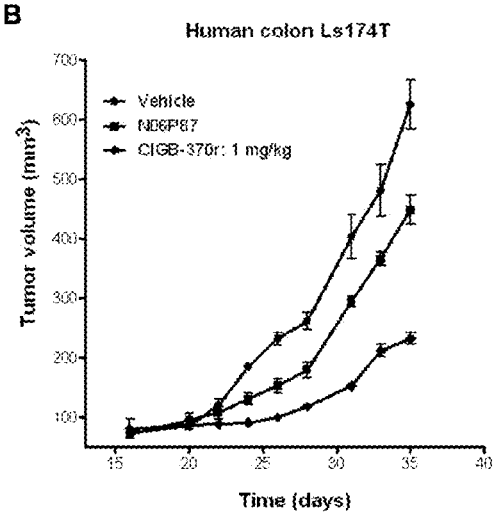
Figure 8:
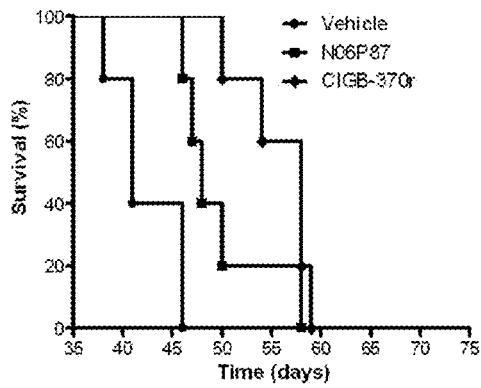

FIG. 8 C shows the survival among animals treated with these molecules or receiving the vehicle. Both molecules were able to significantly increase survival (Logrank test: $p<0.05$) in animals treated, compared to the group receiving the vehicle. Nevertheless, for the case of the N06P87 peptide, the T/C ratio (where T is the mean survival of treated animals and C that of animals only receiving the vehicle) was 117%. This indicated that this linear peptide is not qualified for a potentially useful molecule for cancer therapy in humans, where the T/C ratio has to be at least of 120%. In the case of the CIGB370r polypeptide, it showed a 142% T/C ratio, having the behavior expected from a molecule potentially useful for human cancer therapeutics.

The peptide not even qualified when the T/C ratio was calculated referred to the tumor volume on day 35 (the last day in which the animals when all the animals were still alive), showing a 72% T/C ratio, with the same parameter being 35% for the CIGB370r polypeptide. In this case, the T/C ratio characterizes a significantly active compound when ranging below 40-50% (Marie Suggitt and Michael C. Bibby. 50 Years of Preclinical Anticancer Drug Screening: Empirical to Target-Driven Approaches *Clinical Cancer Research*. 2005. Vol. 11, 971-981.). That indicated that the peptide sequence being identified required further optimization, for a prolonged survival similar to that achieved by the CIGB370r polypeptide and to support its further therapeutic use.

Example 7

Defining the Residues/Regions Functional on the N06P87 Peptide

Figure 9:
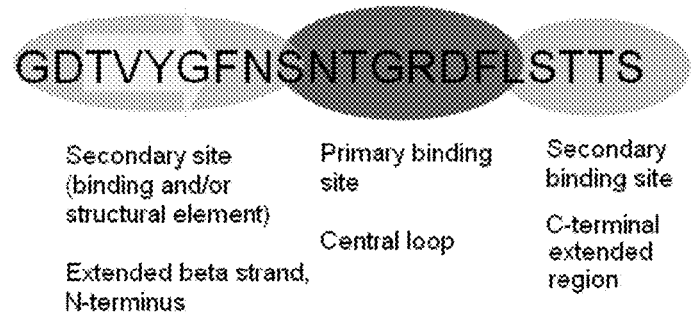
FIG. 9. Definition of functional regions on the segment $Gly_{255}$-$Ser_{274}$ (N06P87 linear peptide). The primary segment of the peptide is the central region, flanked by the secondary N- and C-terminal segments.

The experimental results presented in Examples 2 and 4, together with the tridimensional structural analysis of the p50 protein (Example 3 and the section Detailed description of the invention) allow to define three segments or distinctive regions in the chemical structure of the N06P87 peptide according to their impact on the structure-function relationship of the peptide: a) primary binding region (central loop); b) secondary binding region at the C-terminus; and c) secondary N-terminus region, for binding and/or structural support. This is schematically depicted in FIG. 9. The central loop contains the Gly266-Asp268 segment essential for its biological activity, as well as Phe269 and Leu270 residues which increase its exposure both in p25 and p50. The C-terminus region is a loop adopting an extended conformation in the p50 protein. Residues on this segment apparently participate in the interaction with the receptor, as shown in Example 4, where the C-terminus amide group of the N06P87 peptide is substituted by a carboxyl group, resulting in the loss of the biological activity. Such modification implies the introduction of a new local positive charge, and also the loss of a hydrogen bridge donor group in the peptide. It is also possible that this region could play a structural role: a) Leu270 establishes hydrophobic interactions with Phe269, Tyr259 and the aliphatic side chain of the Arg267 at the central loop; b) Thr272 establishes hydrophobic contacts with Phe261 on the N-terminus region; and c) Ser271 forms three hydrogen bridges with residues on the central loop, the Ser271 amino group is donor of hydrogen bridges for the Arg267 carbonyl group, and the OG group on the side chain of Ser271 is also donor for the Arg267 carbonyl and acceptor of the OH group for the Thr265 side chain. The N-terminus segment plays a structural role: main chain hydrogen bridges of Asp256 (carbonyl group) and Val258 (amino group) with the atoms of the ND2 and OD1 side chains of the Asn264 residue, the carbonyl group (acceptor) of residue Val258 as amino donor (main chain) for Asn264 and the OG atom of Ser263.

Example 8

Introduction or Structural Constraints, Cyclization, Side-Chain Bonds and/or Non-Natural Amino Acids A key aspect for designing strong anticancer drugs of the present invention comprise peptides being designed cyclic, that is, they contain amino acids coupled by means of covalent bonds involving chemical groups on the side chains and/or the amino and carboxyl termini. Therefore, the peptides designed herein are structurally constrained by means of cyclization, which significantly reduces the structural flexibility of these molecules. Generally, the use of peptides as therapeutic agents imposes a number of disadvantages. That is the case of the intrinsic flexibility of peptides; especially the short- and medium-sized, which are more flexible than folded proteins. That is why their process of binding to proteins or any other receptor macromolecules is usually limited by a higher loss of conformational entropy. This fact contributes to these molecules displaying as a rule a binding affinity lower than that of the protein-protein interaction. The lower affinity exhibited by peptides (and consequently lower potency) can be also associated to the fact that the peptide-receptor contact surface is smaller compared to that required for the protein-receptor interface, particularly when peptides comprise the segment of a native protein. For these reasons, it is generally required to redesign and chemically modify peptides to increase their affinity for receptor binding (and consequently potency).

In the present invention, peptide cyclization is preferentially introduced by means of: a) amide bonds between side chains of Lys and Asp/Glu (peptides 5-16, 19-22, 40-43 in Table 5) or between the side chain of Lys and the carboxyl terminus group (peptide 32); and b) introducing disulfide bridges (peptides 1-4, 17-18, 23-31, 33-39, 44-50). Table 5 shows sequences of representative peptides.

TABLE 5

Design of cyclic peptides analogous to the linear N06P87 peptide

| Number | Amino acid sequence*/ Structure | Type of cycle/ Bond |
|---|---|---|
| 1. | CNTGRDFLC | disulfide |
| 2. | GDTVYGFNCNTGRDFLCTTS | disulfide |
| 3. | GDTVCGFNSNTGRDFCSTTS | disulfide |
| 4. | GDTVYGCNSNTGRDFLSTGC | disulfide |
| 5. | GDTVYGFNkNTGRDFLdTTS | amide/side chain |
| 6. | GDTVYGFNkNTGRDFLeTTS | amide/side chain |
| 7. | GDTVYGFNdNTGRDFLkTTS | amide/side chain |
| 8. | GDTVYGFNeNTGRDFLkTTS | amide/side chain |
| 9. | GDTVkGFNSNTGRDFdSTTS | amide/side chain |
| 10. | GDTVkGFNSNTGRDFeSTTS | amide/side chain |
| 11. | GDTVdGFNSNTGRDFkSTTS | amide/side chain |
| 12. | GDTVeGFNSNTGRDFkSTTS | amide/side chain |
| 13. | GDTVYGkNSNTGRDFLSTGd | amide/side chain |
| 14. | GDTVYGkNSNTGRDFLSTGe | amide/side chain |
| 15. | GDTVYGdNSNTGRDFLSTGk | amide/side chain |
| 16. | GDTVYGeNSNTGRDFLSTGk | amide/side chain |
| 17. | GDTVYGCNSNT-(dA)-RDFLSTGC | disulfide |
| 18. | GDTVYGCNSNTGRDFLSTTSC | disulfide |
| 19. | GDTVYGkNSNTGRDFLSTTSd | amide/side chain |

TABLE 5-continued

Design of cyclic peptides analogous to the linear N06P87 peptide

| Number | Amino acid sequence*/Structure | Type of cycle/Bond |
|---|---|---|
| 20. | GDTVYGkNSNTGRDFLSTTSe | amide/side chain |
| 21. | GDTVYGdNSNTGRDFLSTTSk | amide/side chain |
| 22. | GDTVYGeNSNTGRDFLSTTSk | amide/side chain |
| 23. | GDTVYGCNSNT-(dA)-RDFLSTTSC | disulfide |
| 24. | GDTVYGCNSNTGRDFLSTGCK | disulfide |
| 25. | GDTVYGCNSNT-(dA)-RDFLSTGCK | disulfide |
| 26. | GDTVYGCNSNTGRDFLSTTSCK | disulfide |
| 27. | GDTVYGCNSNT-(dA)-RDFLSTTSCK | disulfide |
| 28. | GDTVY-(dA)-CNSNT-(dA)-RDFLSTGC | disulfide |
| 29. | GDTVY-(dA)-CNSNT-(dA)-RDFLSTGCK | disulfide |
| 30. | GDTVY-(dA)-CNSNT-(dA)-RDFLSTTSC | disulfide |
| 31. | GDTVY-(dA)-CNSNT-(dA)-RDFLSTTSCK | disulfide |
| 32. | GDTVYGkNSNTGRDFLSTTN-co- | amide/carboxyl terminus-side chain |
| 33. | GDTVYGkNSNTGRDFLSTTS**-co-** | amide/carboxyl terminus-side chain |
| 34. | (PEG)-GDTVYGCNSNTGRDFLSTGC | disulfide |
| 35. | GDTVYGCNSNTGRDFLSTGCQ | disulfide |
| 36. | GDTVYGCNSNTGRDFLSTGCN | disulfide |
| 37. | GDTVYGCNSNTGRDFLSTGCR | disulfide |
| 38. | GDTVYGCNSNTGRDFLSTTSCQ | disulfide |
| 39. | GDTVYGCNSNTGRDFLSTTSCN | disulfide |
| 40. | GDTVYGCNSNTGRDFLSTTSCR | disulfide |
| 41. | GDTVYGkNSNTGRDFLSTTSeK | amide/side chain |
| 42. | GDTVYGkNSNTGRDFLSTTSeQ | amide/side chain |
| 43. | GDTVYGkNSNTGRDFLSTTSeN | amide/side chain |
| 44. | GDTVYGkNSNTGRDFLSTTSeR | amide/side chain |
| 45. | CNT-(dA)-RDFLC | disulfide |
| 46. | GDTVY-(dA)-C-(dQ)-SNT-(dA)-RDFLSTGC | disulfide |
| 47. | GDTVY-(dA)-C-(dQ)-SNT-(dA)-RDFLSTGCK | disulfide |
| 48. | GDTVY-(dA)-C-(dQ)-SNT-(dA)-RDFLSTTSC | disulfide |
| 49. | GDTVY-(dA)-C-(dQ)-SNT-(dA)-RDFLSTTSCK | disulfide |
| 50. | GDTVY-(dA)-F-(dQ)-CNT-(dA)-RDFLCTTSK | disulfide |
| 51. | GDTVC-(dA)-F-(dQ)-SNT-(dA)-RDFCSTTS | disulfide |
| 52. | Lip-G-CNTGRDFLC | disulfide |
| 53. | CNTGRDFLC-G-lip | disulfide |
| 54. | GDTVYGCNSNTGRDFLSTAC | disulfide |

TABLE 5-continued

Design of cyclic peptides analogous to the linear N06P87 peptide

| Number | Amino acid sequence*/ Structure | Type of cycle/ Bond |
|---|---|---|
| 55. | GDTVYGCNSNTGRDFLSTACQ | disulfide |
| 56. | GDTVYGCNSNTGRDFLSTACN | disulfide |
| 57. | GDTVYGCNSNTGRDFLSTACR | disulfide |
| 58. | GDTVYGCNSNTGRDFLSTACK | disulfide |
| 59. | GDTVYGCNSNTGRDFLSTTC | disulfide |
| 60. | pGlu-GDTVYGCNSNTGRDFLSTGC | disulfide |
| 61. | Acetil-GDTVYGCNSNTGRDFLSTGC | disulfide |
| 62. | (PEG)-GDTVYGCNSNTGRDFLSTGC-(PEG) | disulfide |
| 63. | GDTVYGCNSNTGRDFLSTGC-(PEG) | disulfide |
| 64. | -$X_3X_4$NTGRDFL$Z_1Z_2$- | amide/main chain |
| 65. | -L-(dS)-PTPNTGRDF- | amide/main chain |
| 66. | -L-(dS)-PTPNT-(dA)-RDF- | amide/main chain |
| 67. | (dA)-DTVYGCNSNTGRDFLSTGC | disulfide |
| 68. | -DFLST-P-(dA)-Q-NSNTGR- | amide/main chain |
| 69. | -DFLSR-P-(dA)-Q-NSNTGR- | amide/main chain |
| 70. | -L-(dA)-PTPNTGRDF- | amide/main chain |
| 71. | -L-GPTPNTGRDF- | amide/main chain |
| 72. | -DFLST-P-G-Q-NSNTGR- | amide/main chain |
| 73. | -DFLSR-P-G-Q-NSNTGR- | amide/main chain |
| 74. | -DFLSR-P-(dA)-($_{Bm}$Q)-($_{Nm}$N)-SNTGR- | amide/main chain |
| 75. | -DFLST-P-(dA)-($_{Bm}$Q)-($_{Nm}$N)-SNTGR- | amide/main chain |
| 76. | -DFLS-R-R-P-NSNTGR- | amide/main chain |
| 77. | -DFLS-K-K-P-NSNTGR- | amide/main chain |

*unless specified some modification, the C-terminus is amidated and the N-terminus is free;
-covalent bond, (a) if the dash appears on the terminus of the sequence it means that the terminus group is modified by a covalent bond to a substituent or polymer,
(b) two dashes, one at the N-terminus and another at the C-terminus, indicate that the peptide is cyclic by forming an amide bond between the amino and carboxyl groups of the main chain of termini residues; and
(c) a dash in the middle of any sequence stands for a peptide bond;
k, Lys residue which side chain forms an intramolecular amide bond;
d, Asp residue which side chain forms an intramolecular amide bond;
e, Glu residue which side chain forms an intramolecular amide bond;
-co-, carboxyl terminus covalently linked by an intramolecular amide bond to a Lys side chain;
dA, the stereoisomer D-Ala;
dQ, the stereoisomer D-Gln;
dS, the stereoisomer D-serine;
(PEG)- and (PEG), pegylation at the amino terminus and carboxyl terminus, respectively;
pGlu, pyroglutamic acid;
$X_3X_4$ and $Z_1Z_2$, dipeptides;
$_{Bm}$Q, L-b-methylglutamine (Gln methylated in the beta carbon);
$_{Nm}$N, N-methyl Asn.

TABLE 6

Especial amino acids susceptible to be used analogous to residues Lys and Asp/Glu for cyclization of side chains and/or chemical modification of the peptide by covalent linkage to a polymer or side chain

| No | Amino acid | Functional group |
|---|---|---|
| 1. | 2-[bis(3-aminopropyl)amino]acetic acid | NH2 |
| 2. | (2S)-2,5-diaminopentanoic acid | NH2 |
| 3. | 2,2-diaminoacetic acid | NH2 |
| 4. | (3S)-3,4-diaminobutanoic acid | NH2 |
| 5. | (2R)-2,4-diaminobutanoic acid | NH2 |
| 6. | (2S)-2,4-diaminobutanoic acid | NH2 |
| 7. | (2S)-2,3-diaminopropanoic acid | NH2 |
| 8. | (2R)-2,3-diaminopropanoic acid | NH2 |
| 9. | 2-[(2-aminoethyl)amino]acetic acid | NH2 |
| 10. | 2-[(3-aminopropyl)amino]acetic acid | NH2 |
| 11. | 2-[(4-aminobutyl)amino]acetic acid | NH2 |
| 12. | (4S)-4,8-diaminooctanoic acid | NH2 |
| 13. | (2S)-2-amino-3-(4-aminophenyl)propanoic acid | NH2 |
| 14. | (2S)-2-amino-3-[4-(2-aminoetoxi)phenyl]propanoic acid | NH2 |
| 15. | 2-(piperidin-4-yl amino)acetic acid | NH |
| 16. | (2S)-2-amino-4-[(5R)-2,2-dimethyl-1,3-oxazolidin-5-yl]butanoic acid | NH |
| 17. | (2S)-2-amino-6-(methylamino)hexanoic acid | NH |
| 18. | (2R,4R)-4-aminopyrrolidine-2-carboxylic acid | NH |
| 19. | (2R,4S)-4-aminopyrrolidine-2-carboxylic acid | NH |
| 20. | 2-(4-aminopiperidin-4-yl)acetic acid | NH |
| 21. | 4-aminopiperidin-4-carboxylic acid | NH |
| 22. | (2S,4R)-4-aminopyrrolidine-2-carboxylic acid | NH |
| 23. | Imidazolidine-2-carboxylic acid | NH |
| 24. | 3-[(carboxymethyl)amino]propanoic acid | COOH |
| 25. | 2-[(carboxymethyl)amino]acetic acid | COOH |
| 26. | 3-[(2-carboxyethyl)amino]propanoic acid | COOH |
| 27. | (3R)-3-aminohexanodioic | COOH |
| 28. | 4-aminoheptanodioic acid | COOH |
| 29. | 4-aminopiperidin-1,4-dicarboxylic acid | COOH |
| 30. | (2S,4S)-4-aminopyrrolidine-2-carboxylic acid | COOH |
| 31. | 2-[(carboxymethyl)amino]acetic acid | COOH |
| 32. | (2S)-2-amino-6-[(carboxymethyl)amino]hexanoic | COOH |
| 33. | 3-[(2-carboxyethyl)amino]propanoic acid | COOH |
| 34. | (2S)-2-aminoheptanodioic acid | COOH |
| 35. | (2S)-2-aminooctanodioic acid | COOH |
| 36. | (2R)-2-amino-3-[(2-carboxyethyl)sulfanyl]propanoic acid | COOH |
| 37. | (2R)-2-amino-3-[(carboxymethyl)sulfanyl]propanoic acid | COOH |
| 38. | 4-{[(2R)-2-amino-2-carboxyethyl]sulfanyl}butanoic acid | COOH |
| 39. | (2S)-2-amino-3[4-(carboxymethoxy)phenyl]propanoic acid | COOH |

TABLE 7

Special amino acids susceptible to be used analogous to cystein for peptide cyclization by means of disulfide bridges and/or for peptide chemical modification by linkage to a polymer by the side chain.

| No | Amino acid |
|---|---|
| 1. | (2R)-2-amino-3-sulfanylbutanoic acid |
| 2. | (2R)-2-amino-3-methyl-3-sulfanylbutanoic acid |
| 3. | (2S)-2-amino-4-sulfanylbutanoic acid |
| 4. | 2-amino-5-sulfanyl-pentanoic acid |
| 5. | 2-amino-3-sulfanyl-pentanoic acid |
| 6. | 2-amino-4-methyl-3-sulfanylpentanoic acid |
| 7. | 2-amino-3-methyl-4-sulfanylpentanoic acid |
| 8. | 2-amino-3,4-dimethyl-3-sulfanyl-pentanoic acid |
| 9. | 2-amino-3-ethyl-3-sulfanylpentanoic acid |
| 10. | (2R)-2-amino-3-methyl-3-sulfanylpentanoic acid |
| 11. | (4S)-4-amino-2-methyl-5-sulfanylpentanoic acid |
| 12. | (4R)-4-amino-2-metil-5-sulfanylpentanoic acid |
| 13. | (4R)-4-amino-5-sulfanylpentanoic acid |
| 14. | (4S)-4-amino-5-sulfanylpentanoic acid |

In all the cases, the structural constraints introduced in the structure of the designed peptide have to be compatible with the biologically active conformation of the molecule. Therefore, the design of cyclizations of the present invention includes both the selection of potential positions on the sequence for substitution/introduction of aminoacids to be linked by side chains (replacement positions) and the type(s) of amino acid(s) to be introduced (linkage residues). The inter-residue distances corresponding to replacement positions on the peptide have to be compatible with the strereochemical nature of the linkage residues selected. In the specific case of introducing disulfide bridges, for example, there are not considered as potential replacement positions those residues which distances between the alpha carbons are higher than 7 Å or lower than 3.8 Å in the active conformation (Vardhan S. Dani, C. Ramakrishnan and Raghavan Varadarajan. Protein Engineering vol. 16 no. 3 pp. 187-193, 2003). Similarly, positions with distances between beta carbons between 3.6 Å and 4.7 Å are regarded as preferred. Stereochemical descriptors art replacement positions, such as alpha and beta carbons, should support torsion angles at the lateral chains of linkage residues enough to adopt favorable values once established the covalent bond between the residues, what indicates the existence of favorable non-covalent interactions (van der Waals).

The following steps were considered for the design of the peptides cyclized by disulfide bridges (by cysteins) of the present invention: a) selection of potential replacement position pairs of the N06P87 peptide able to be substituted by cysteins linked by disulfide bridges, b) tridimensional structure modeling of the modified peptides/minimized energy of the models and c) evaluation of the energy and/or stereochemical quality parameters of the models. Replacement positions for cysteins on the N06P87 peptide were selected by using the MODIP (Vardhan S. Dani, C. Ramakrishnan and Raghavan Varadarajan. Protein Engineering vol. 16 no. 3 pp. 187-193, 2003), a software developed for designing protein disulfide bridges. The method assigns a score to potential disulfide bridges, by using an empirical energy depending on the inter-atomic distances for alpha and beta carbons, and also the values for the torsion angles $\chi^1$, $\chi^2$, $\chi^{SS}$, $\chi^{1'}$ and $\chi^{2'}$ (R. Sowdhamini, N. Srinivasan, B. Shoichet, D. V. Santi, C. Ramakrishnan and P. Balaram (1989). Prot. Engng., 3, 95-103). Depending on the energy values calculated for the potential disulfide bridges, MODIP assigns a quality score of A (ideal stereochemistry), B (of proper geometry but having stereochemical torsion) or C (closely enough to allow the formation of disulfide bridges), where A represents the highest quality and C the lowest. The 3D structural models of the designed peptides were obtained by using molecular modeling software and (preferentially) can be obtained by Nuclear Magnetic Resonance. In the present invention, the MODELLER software was used to model the peptides (Sali A, Blundell T L, 1993, J Mol Biol 234:779-815) y WHATIF (Vriend G, 1990, J Mol. Graph. 8(1):52-6, 29).

The crystallographic structure of the p50 was used as starting point for this analysis—file PDB 1SRP. As previously discussed in the section Detailed description of the invention, experimental Data suggest that the biologically active conformation of the N06P87 peptide is similar to that adopted by the Gly255-Ser274 fragment in the p50/p25 protein. Table 8 shows the results for the prediction of potential replacement positions in this segment.

TABLE 8

Prediction of replacement positions for cysteins linked by disulfide bridges in the N06P87 peptide with the aid of MODIP

| No. | Residue i | | Residue j | | Degree[§] |
|---|---|---|---|---|---|
| 1* | PHE | 7 | SER | 20 | C |
| 2 | THR | 11 | LEU | 16 | A |
| 3 | SER | 9 | SER | 17 | A |
| 4 | TYR | 5 | LEU | 16 | B |

*Prediction was made for a model of the N06P87 peptide modified by the Thr$_{19}$→Gly substitution;
[§]Degree of stereochemical quality for the predicted disulfide bridge, A the highest, C the worst.

Figure 10:
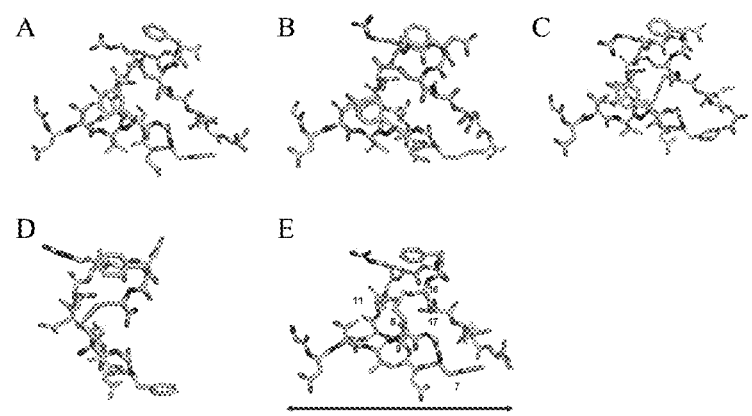
FIG. 10. Modeling of the cyclic peptides J08P48s-s, A08P28s-s, A08P25s-s, J08P46s-s and the linear peptide N06P87 of the present invention, designed from the $Gly_{255}$-$Ser_{274}$ segment of the p50 protein. Models were obtained with the aid of the MODELLER software, by using the crystallographic structure of the p50 protein as a pattern. Disulphide bridges were introduced at positions previously identified by the MODIP method. A: modeling of N06P87 (linear peptide) according to the tridimensional (3D) structure of the $Gly_{255}$-$Ser_{274}$ segment on the p50 protein; B: modeling of the J08P48s-s peptide; C: modeling of the A08P28s-s peptide; D: modeling of the A08P25s-s peptide; E: modeling of the J08P46s-s peptide, indicating the distance between the N- and C-termini of the peptide.

Pairs 2-4 are predicted from the native structure and show A and B quality scores, while the pair 1 requires a slight conformational change on the T$_{19}$ residue and thus, the resulting disulfide bridge has a lower quality. Hence, the present invention includes peptides containing the T$_{19}$→G or T$_{19}$→A substitutions to favor the adoption of a favorable conformation for establishing the disulfide bridge. The substitution of Gly allows increasing the local flexibility, favoring conformational changes at the carboxyl terminus aiding the formation of the bridge. The substitution of Ala is adequate, considering its favorable propensity of this residue to adopt helicoidal conformations, as the one predicted for the residue 19 according to the models obtained for the structure of peptide 4 in Table 5 (phi-psi torsion angles of the model -69, -38). The introduction of Ala, compared to the T$_{19}$→G substitution, is characterized by a lower loss of configuration entropy during folding and/or receptor binding. FIG. 10 shows the models for a group of cyclic peptides designed from the MODIP prediction shown in Table 8.

Figure 11:
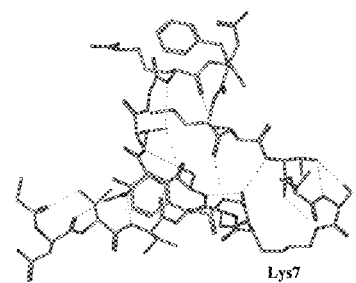
FIG. 11. Structure modeling of the cyclic peptide 33 in Table 5. Lysine 7 forms an amide bond with the carbonyl terminal group.

The same replacement positions used to design the disulfide bridges are also appropriate for designing the cyclic peptides with linkage residues forming amide bonds, as Lys and Asp/Glu residues. Since the number of atoms linking the alpha carbons of linkage residues is higher in this case than those existing in the disulfide bridges, the stereochemical restrictions determining their introduction in the design of the peptides are less restrictive and therefore the replacement positions predicted with MODIP are also adequate as a primary approach. Once selected a pair or residues for a given bond, the resulting peptide is modeled and evaluated energetically (and/or evaluated the quality according to the stereochemical parameters). The peptide 33 in Table 5 was designed by a similar protocol, this peptide containing an amide bond between Lys7 and the terminus carbonyl group (FIG. 11).

Another cyclization method preferred by the present invention comprises the introduction of a covalent bond between the amino and carbonyl groups of the N- and C-termini of peptides. The stereochemical restrictions of the peptide bond make necessary to introduce aa. connectors, which facilitates adopting a structure compatible with the biological activity of peptides. For example, the higher the distance between the alpha carbons of the "anchor" residues in the 3D structure of the p25/p50 protein to be linked (d$_{CA-CA}$) compared to the 3.9 Å distance existing between CA of a peptide unit, the higher the number of connector residues (N$_{con}$) required. If adequate connector residues are not introduced between two anchor residues to suffice the respective distance restrictions, it is highly probable that the peptide could not adopt the experimentally observed conformation, this very likely having a negative effect on the biological activity. The connector residues were designed according to the following protocol:

I. Selection of N06P87 peptide residues to be connected: neighboring residues in the 3D structure, preferentially those not included in the segment of primary binding or primary segment;
II. Identification of the minimal number of connector residues required: $N_{con} > d_{CA-CA}/3.9$;
III. Selection of anchoring residues: N06P87 peptide residues to be connected and the neighboring ones, with 2-3 residues being selected at both termini;
IV. Search for segments of N residues ($N_{con}+4 > N > N_{con}+6$) in a non-redundant 3D protein structure database, in a way that the main chain structure of the 2-3 residues at the fragment termini will be similar to the structure of the anchoring residues;
V. Selection of the sequence and structure of the connector segment: the structure of the most common connector segment observed in step IV is selected and the parameters of choice are calculated for each amino acid in every position, that is, the ratio between the number of amino acid appearances and the value expected according to the relative abundance of the amino acid in the database. Amino acids (one or several) showing the highest preference parameters are selected for each position. It is possible to modify the residues neighboring the connector segment following the criterion of the highest value of the preference parameter. In those cases involving positions with positive torsion angles is possible to introduce D-stereoisomers. It is also possible to introduce other non-natural amino acids (such as beta- and N-methylated amino acids) for increasing the structural propensity of the residue to adopt the adequate conformation on the main chain for the structure required.

Figure 12:
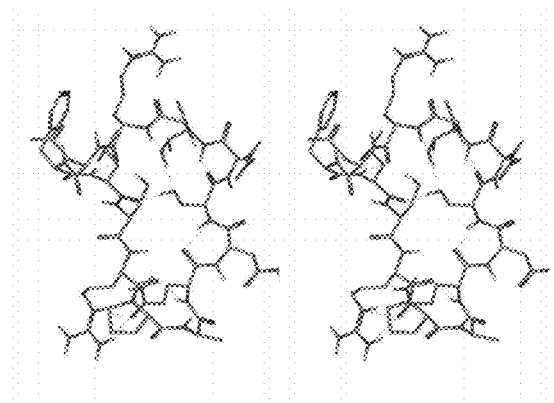
FIG. 12. Stereoscopic image of structure modeling of the cyclic peptide 69 in Table 5. The primary segment Asn264-Ser271 is cyclized by the hexapeptide connector Arg-Pro-(dAla)-Gln-Asn-Ser. The residue dAla is the D-Ala stereoisomer.

Since these peptides are cyclized by amide bonds between the N- and C-termini, cyclic permutations of the sequence comprise identical peptides. In an example of the present invention, peptides are designed based on the primary binding segment defined for the N06P87 peptide, and said segment is connected by a tetrapeptide (two dipeptides) of general sequence $Z_1Z_2X_3X_4$ (or $X_3X_4 y Z_1Z_2$ respectively, peptide 64 in Table 5). These peptides contain up to 11 amino acids. The connector sequences of the present invention can also include D-aa. at those positions which residues adopt positive torsion angles (peptides 65 and 66 in Table 5). The sequence of the connector tetrapeptide is preferentially, but not exclusively, dSer-Pro-Thr-Pro (peptide 65 in Table 5, dS is the D-Ser stereoisomer), although it could also be Gly-Pro-Thr-Pro (peptide 71 in Table 5) or dAla-Pro-Thr-Pro (peptide 70 in Table 5, dAla is the D-Ala stereoisomer). In another exemplification, the peptides of the present invention comprise the sequence corresponding to the Asn262-Ser271 segment of the p50 polypeptide, connected by a tetrapeptide. The resulting peptides have 14 residues. The preferred sequence of the tetrapeptide connector can be—but not exclusively—Thr-Pro-Gly-Gln (peptide 72 in Table 5), alternatively—but not exclusively—Arg-Pro-(dAla)-Gln (peptide 69, see FIG. 12) or Arg-Pro-Gly-Gln (peptide 73 in Table 5), or Thr-Pro-(dAla)-Gln (peptide 68 in Table 5). Therefore, the sequence of these peptides can be described as the segment Asn264-Ser271 cyclized by means of a connector hexapeptide which sequence is preferentially: (Thr o Arg)-Pro-(Gly or dAla)-Gln-Asn-Ser. Alternatively, residues 4 and 5 in the hexapeptide connector can be respectively aminoacids $_{Bm}$Gln and $_{Nm}$Asn, where $_{Bm}$Gln and $_{Nm}$Asn are aminoacids L-b-methylglutamine (L-glutamine methylated on its beta carbon) and L-n-methyl asparagine (N-methyl L-asparagine), respectively. The betamethylated aminoacids are more prone to adopt extended conformations (beta-like structures) and the N-methylated to adopt polyproline-like structures, which are the structures adopted by residues 4 and 5 in the model structures of the peptide obtained by the protocol described (steps I-IV) for designing of connector segments.

Figure 13:
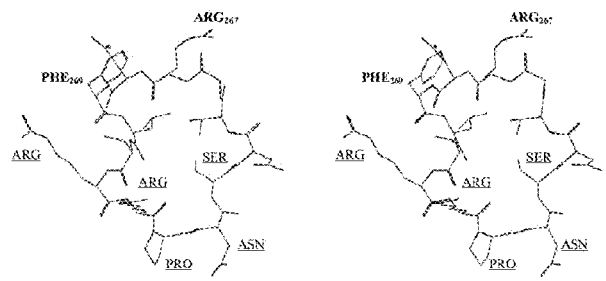
FIG. 13. Stereoscopic image of structure modeling of the cyclic peptide 76 on Table 5. The primary segment Asn264-Ser271 is cyclized by the pentapeptide connector Arg-Arg-Pro-Asn-Ser (underlined residues).

Another exemplification of the present invention consists on peptides which sequence corresponds to the Asn262-Ser271 segment of p50 connected by a tripeptide (or analogously the segment Asn264-Ser271 connected by a pentapeptide). The tripeptide connector preferentially has—but nor exclusively—the sequence (Arg or Lys)-(Arg or Lys)-Pro (peptides 76-77 in Table 5, FIG. 13), the respective pentapeptide connector having the sequence (Arg or Lys)-(Arg or Lys)-Pro-Asn-Ser.

Example 9

Stereoisomers

Figure 14:
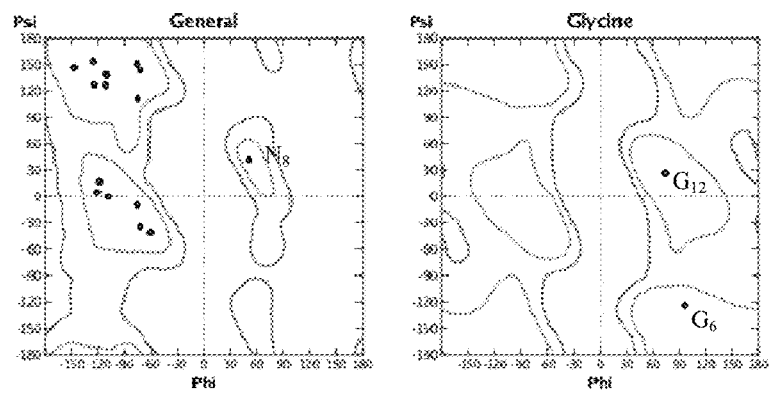
FIG. 14. Ramachandran diagram corresponding to the 3D structure of the segment Gly255-Ser274 of the p50 protein.

For the purpose of increasing the structural stability and, consequently, the affinity/potency of peptides, a modification considered in the present invention comprises the substitution of natural L-amino acids in the original N06P87 sequence by their respective stereoisomers (D-amino acids, D-aa.). Since D-aa. adopt favorable positive torsion angles, the N06P87 residues candidate to be substituted are those adopting such torsion angles in the structure of the native protein (and/or structural models of the peptides). FIG. 14 shows the Ramachandran diagram corresponding to the 3D structure of the $Gly_{266}$-$Ser_{274}$ segment of p50. With the aid of definitions of Ramachandran diagram regions definition of Rooman and Wodak (Rooman M J, Kocher J P, Wodak S J. 1991. J Mol. Biol. 221(3):961-79), residues $N_8$ and $G_{12}$ are located in the L region (helicoidal region with left-handed rotation) and $G_6$ in the extended conformation E region ($G_6$ phi and psi values are also prohibitive for the rest of L-amino acids). Therefore, the substitution of $N_8$, $G_{12}$ and $G_6$ by D-Ala is favorable considering the propensity of this residue to adopt such main chain conformations and/or to decrease the folding/binding-associated loss of configuration entropy. Since residues L-Glu, L-Gln and L-Asp are highly prone to adopt helicoidal conformations (right-handed rotations) when these residues are located in protein loops (Swindells M B, MacArthur M W, Thornton J M. 1995. Nat Struct Biol. 2(7):596-603), by analogy, D-Glu, D-Gln and D-Asp are prone to adopt helicoidal conformations of left-handed rotation (as in the case of the $N_8$ residue). Peptides 17, 23, 25, 27-31, 45-51 (Table 5) bear from one to three D-aa. designed according to previously mentioned criteria. The introduction of D-aa. in the structure of the peptides of the present invention also has a favorable effect on the conformation, and therefore, on affinity, positively contributing to the pharmacokinetic properties of the peptides by increasing their resistance to proteolysis in vivo based on two main reasons: a) a direct effect, since serum endoproteases digest stereo-specific substrates; and b) the lower flexibility of the peptides making them less susceptible to proteolytic digestion.

Example 10

Blocking the Peptide Termini and/or Conjugation to Polymers

Peptides are characterized by a lower mean half-life time in vivo (lower size, renal exclusion), the highest flexibility also implicating increased susceptibility to proteolysis, and therefore lower bioavailability. Hence, the introduction of chemical modifications in the peptides could be advised for to improve their bioavailability. The present invention includes the design of covalently modified peptides with polyethylene glycol chain(s) (PEGS), preferably by modifying the peptide termini, but not without excluding other modifications, as, for example, side chains. Examples of pegylated peptides of the present invention are shown in Table 5 (peptides 62 and 63). Pegylated peptides of the present invention, therefore, show a better profile of resistance to proteolysis, reduced renal filtration, lower probability of interaction with antibodies and subsequent neutralization of its activity, and decreased antigenicity and immunogenicity.

Pegylation increases the circulation time of small molecules, small peptides being excreted rapidly, been reported as having renal toxicity frequently when radio-labeled (Blumenthal R. D., Sharkey R. M., Goldenberg D. M. Goldenberg D. M. eds. Cancer Therapy with Radiolabeled Antibodies, 295-314, CRC Press Boca Raton, Fla. 1995.). Pegylation have been used to modify synthetic drugs, as interferons and antibodies. The present invention includes the presentation of peptides by means of designing multimeric structures, using linear or branched PEGS which allow higher avidity for peptide-receptor binding.

Pegylation increases the apparent molecular size of peptides, reducing the renal filtration rate (Knauf M. J., Bell D. P., Hirtzer P., Luo Z. P., Young J. D., Katre N. V. J. Biol. Chem., 263: 15064-15070, 1988; Behr T. M., Goldenberg D. M., Becker W. Eur. J. Nucl. Med., 25: 201-212, 1998). The peptides of the present invention are modified preferably with PEGs increasing their molecular size to values equal or above 50 kDa, to drastically reduce the glomerular filtration of the molecule.

Pegylation, in addition to increasing the circulation time, reduces the antigenicity and susceptibility to proteolysis of therapeutic molecules (Delgado C., Francis G. E., Fischer D. Crit. Rev. Ther. Drug Carrier Syst., 9: 249-304, 1992.), and induces an increase in their solubility and vascular permeability (Francis G. E., Delgado C., Fisher D., Malik F., Agrawal A. K. J. Drug Target., 3: 321-340, 1996), a highly desirable property for antineoplastic drugs.

There are several exopeptidases in blood, kidney and liver (Werle M, Bernkop-Schnrch A. Amino Acids. 2006 June; 30(4):351-67), and therefore, modification of the peptide N- and C-termini can significantly increase its proteolytic stability. N-acetylation is a modification recommended in the present invention, and also the introduction of pyroglutamate at the N-terminus, or a D-stereoisomer amino acid, etc. Peptides of the present invention are mostly C-amidated (amide at the C-terminus), which provides them carboxypeptidase resistance.

Modification of the N- and/or C-termini can also be pegylation, which increases the resistance to proteases and particular to exopeptidases by termini modification, in addition to its related and previously mentioned properties related to increased size and reduced antigenicity/immunogenicity. Besides, the addition of PEGS induces an increase in the resistance to proteolysis in general (endo and exo) by esteric hindrance for proteolytic enzymes. For this purpose, PEGS are used either linear or branched.

Cyclization also protects the peptides against exopeptidase proteolysis, by forming a covalent bond between the N- and C-termini previously described (peptides 64-66, 68-69 in Table 5) or by covalent linkage of one termini to a side chain (peptides 32-33 in Table 5). The resistance to exopeptidases is also achieved by substituting the termini amino-acids by D-aa. (peptide 67 in Table 5).

As alternative to modification with PEGs, it is also possible the conjugation to N-acetylneuraminic acid (sialic acid), a polymer naturally occurring and highly hydrophilic, biodegradable, with no receptor in humans, and which can increase the resistance to proteases (plasma stabilization) and the half-life time (Gregoriadis G, Fernandes A, Mital M, McCormack B (2000) Cell Mol Life Sci 57: 1964-1969; Fernandes Al, Gregoriadis G (1997) Biochim Biophys Acta 1341: 26-34). Another plausible modification of the peptides of the present invention comprises the N-terminus substitution by fatty acids or lipidation (peptides 52-353 in Table 5). This strategy increases the resistance of peptides to proteolysis by exopeptidases, and facilitates the interaction of peptides with membranes. Depending on the nature of the lipid it could favor the interaction with certain membrane domains, facilitating the accumulation of the peptides in domains rich on the receptor target of the pharmacological action of the peptides. Lipidation also favors the formation of supramolecular structures of better pharmacokinetic and pharmacodynamic properties (micelles, aggregates, particles, vesicles).

Example 11

Description of the Chemical Structure of Peptides of the Present Invention

Figure 15:
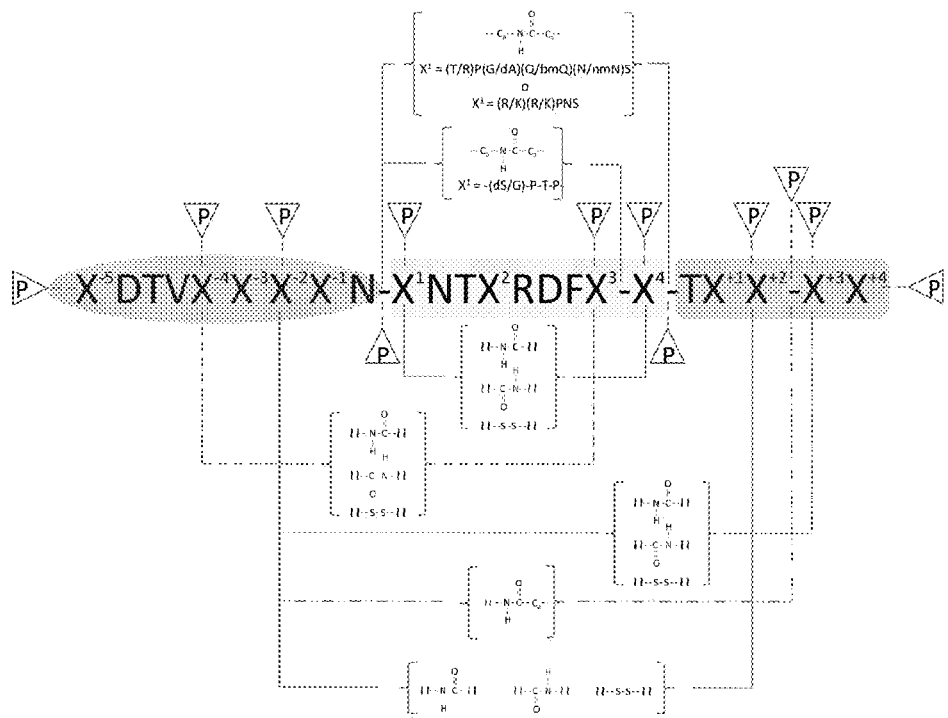
FIG. 15. General diagram of the chemical structure for the designed cyclic peptides of the present invention. Lines indicate the presence of a covalent bond. When connecting two residues of the peptide, lines indicate that those residues are cyclized, i.e., covalently linked. Lines located above the sequence of the peptide correspond to the cyclization of the main chain, and those below represent the bonds for cyclization involving at least one side chain. If a line points towards a $X^i$ residue, it means that the covalent bond is produced by the side chain of that $X^i$ residue. If the line starts at a dash between two residues it means that the covalent bond involves the amino or carbonyl group of the residue following or preceding the dash, respectively. The line pointing to the dash preceding the $X^1$ represents an amide covalent bond comprising the amino group of the $X^1$ residue; in this case the peptide does not have secondary N-terminus. The lines behind $X^4$ and $X^{+2}$ indicate a covalent bond comprising the carbonyl group of $X^4$ and $X^{+2}$, additionally representing the absence of secondary C-terminus behind $X^4$ and that the residue is the carboxyl terminus of the peptide behind the $X^{+2}$. In braces are indicated the groups involved in the covalent bond and the type of bond: amide bonds or disulfide bridges, also showing the preferred sequences for the peptide connectors. The shaded areas on the peptide sequence indicate the order from the N- to the C-termini of the functional segments defined in the invention: (a) secondary N-terminal segment, (b) primary segment and (c) secondary C-terminal segment. Triangle P signals the sites able to be modified by covalent linking to polymers or other chemical groups, such modifications are feasible if the residue or group on the main chain involved does not participate in a cyclization bond. The peptide can bear one or more cyclization bonds, and one or more polymer modifications and/or chemical groups. The amino acid analogues mentioned in the figure as possibly occupying the replacement positions $X^{-4}$, $X^{-2}$, $X^1$, $X^3$, $X^4$, $X^{+2}$ and $X^{+3}$ are amino acids which side chains comprise the amino group or the carboxyl group or the sulfhydryl group.
Figure 16:
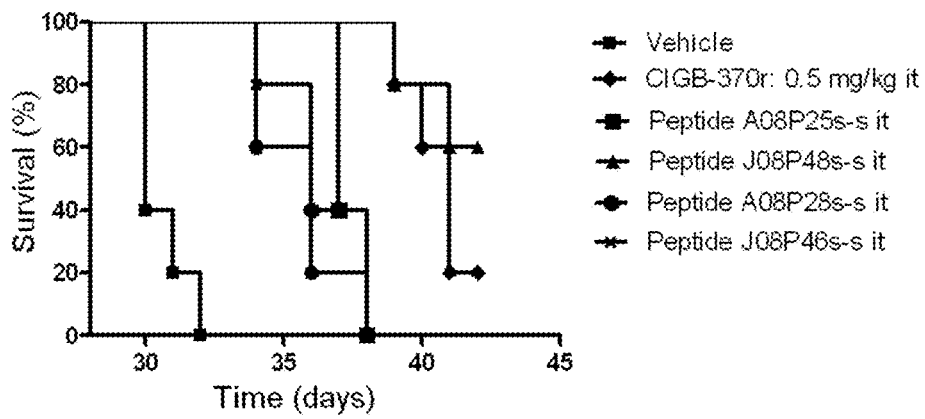
FIG. 16. Optimized cyclic peptides, derived from the p25 polypeptide, increase the survival of treated animals. Animals carrying the subcutaneous TC-1 tumor were injected with a single dose of 80 µM by intratumoral route (i.t.). Each group received a different peptide, or the CIGB370r polypeptide or the excipient. Survival is shown for all the groups.

FIG. 15 shows a general representation of the chemical structure of peptides of the present invention. The design is based, firstly, in the primary segment defined in the realization Example 7. In general, the peptide sequence Asn264-Leu270 is exposed in different structural contexts, all including different constraints degrees, by means of cyclization which involve the main chain and/or the side chains of the peptides. Cyclizations are established by means of bonds of different chemical nature: amide or disulfide bonds, but replacement positions being occupied by the residues of the cyclic side chains and the side chains themselves, are carefully chosen to reproduce the structure and topography of the p50/p25 protein functional site identified in the present invention. A particular solution consists on cyclization of the main chain, carried out by selecting the anchor sites and connector sequences which bear high structural propensity to adopt a conformation compatible with the structure of the primary segment. Secondary segments are also used optionally, mainly for support replacement positions with cyclic side chains. Moreover, secondary segments can provide additional contact surface for interacting with the potential receptors, according to the topography of the p50/25 functional site. An example comprises the inclusion of residues carrying positive charge and/or hydrogen bridges donors at positions $X^{+3}$ and $X^{+4}$ of the C-terminus secondary segment. Peptides can include one or more cycles of those shown in FIG. 15, although only monocycles have been included as examples to be shown in Table 5. The peptides of the present invention can include non-natural or especial aa., which side chains comprise the amino, carboxyl or sulfhydryl groups, aimed at occupying replacement positions for cyclization or any other chemical modification. It could also include D-aa. stereoisomers at the polypeptide chain positions able to adopt positive torsion angles, either for the primary or the secondary segments. Additionally, the peptides of the present invention can be modified by the covalent linkage to polymers, such as PEG and/or other chemical groups. Such modifications can be made at the termini and/or side chains of replacement positions, unless they were occupied by cyclized side chains.

Peptides 1, 2, 3 and 4 in Table 5 (encoded during their synthesis and purification as: A08P25s-s, A08P28s-s, J08P46s-s, and J08P48s-s, respectively) are realization examples covering the essential aspects of the peptides of the invention, including: different sizes, with or without secondary segments and the main replacement positions. These peptides were selected to demonstrate their effects in in vivo tumor models: the structural simulation of the cryptic peptide fragment having cytotoxic activity in the p25 polypeptide generates peptide molecules of up to 20 aa., which effectively reproduce the antitumor activity of p25, advantageously, to be used in cancer therapy.

Example 12

Evaluation of the Antitumor Activity of Optimized Cyclic Peptides in Syngeneic and Xenograft Tumor Models With the aim of evaluating the antitumor activity of the new family of cyclic peptides of the present invention, these peptides mimicking the structure of the active region of the p25 polypeptide, 4 peptide models were selected comprising different cyclization and insertion variants of this family. They were peptides 1, 2, 3 and 4 in Table 5 (coded for the activity assays as A08P25s-s, A08P28s-s, J08P46s-s and J08P48s-s, respectively). As positive control group was used a group treated with the CIGB370r polypeptide.

Six-to-eight weeks-old, C57BL/6 female mice of 22 g of weight were supplied by the National Center for Laboratory Animal Production (CENPALAB, Havana, Cuba) and housed under pathogen-free conditions at the Bioterium of the Center for Genetic Engineering and Biotechnology (CIGB). Experiments were carried out in agreement with regulations for proper handling and care of laboratory animals. Tumor volume was measured on each case (estimated by the formula: volume=$a^2 \times (b/2)$, where a is the width and b is the length of the tumor) and animal survival was evaluated.

Survival was compared between groups by the Logrank test. The statistic parameters were obtained with the aid of the GraphPad Prism 4.0 software (GraphPad Software, San Diego, Calif., USA).

C57BL/6 mice were injected in the right flank by subcutaneous route (s.c.) with 50 000 TC-1 cells. When tumors were detectable, mice were randomized into treatment groups to evaluate the treatment with the peptides subject of study, to evaluate them by different administration routes. Tumor-bearing animals received 6 administrations in alternate days, with 80 µM of the subject peptide, solely received the vehicle as control. Five mice were used for each group. Animals were housed under pathogen-free conditions, and procedures were conducted in agreement with good practices for laboratory animal handling and care.

Survival was statistically significant in all the groups treated, compared to the group receiving the vehicle. FIG. 6 shows 3 blocks: 1) the highest survival block, including the groups treated with peptide J08P48s-s and CIGB370r, respectively, with no statistically significant differences between them; 2) the intermediate survival block, including the groups treated with peptides A08P28s-s, A08P25s-s, and J08P46s-s, respectively, with no statistically significant differences between them, and different from block 1; and 3) the negative control group. These results demonstrate that the new family of peptides described herein, represented by the peptides evaluated in this model, is capable of achieving the activity described for the polypeptide of origin.

Figure 17:
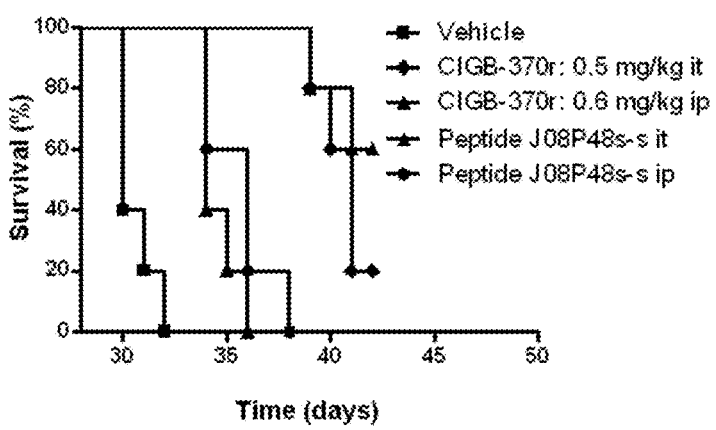
FIG. 17. Optimized cyclic peptides, derived from the p25 polypeptide, increase the survival of treated animals regardless of the administration route. Animals carrying the subcutaneous TC-1 tumor were injected with a single dose of 80 µM by intratumoral (i.t.) or intraperitoneal (i.p.) routes. Each group received different peptide, or the CIGB370r polypeptide or the excipient. Survival is shown for all the groups.

In addition to the intratumoral route, in this TC-1 model were explored other administration routes for the peptides, as the intraperitoneal route. FIG. 17 shows that cyclic peptides, (for example, the J08P48s-s peptide), reproduce the effects observed in this model for the CIGB370r polypeptide when they were administered by both routes. This evidences the effectiveness of the cyclic peptides of the present invention to treat distal solid tumor.

Figure 19:
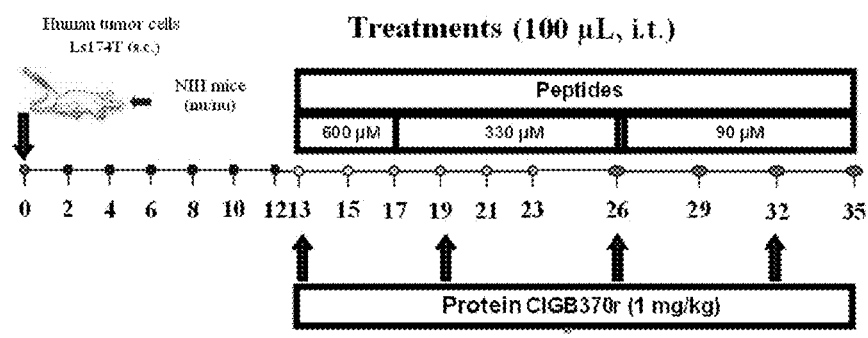
FIG. 19. Optimized cyclic peptides, derived from the p25 polypeptide, increase the antitumor activity and survival in animals treated with the linear peptide, and their activities are analogous to that of the CIGB370r polypeptide. (A) Administration schedule; (B) Antitumor effect as evaluated by measuring tumor volume (B); and Antitumor effect evaluated through the survival of inoculated mice (C). Model: human colon cancer Ls174T implanted in NIH athymic mice.
Figure 19:
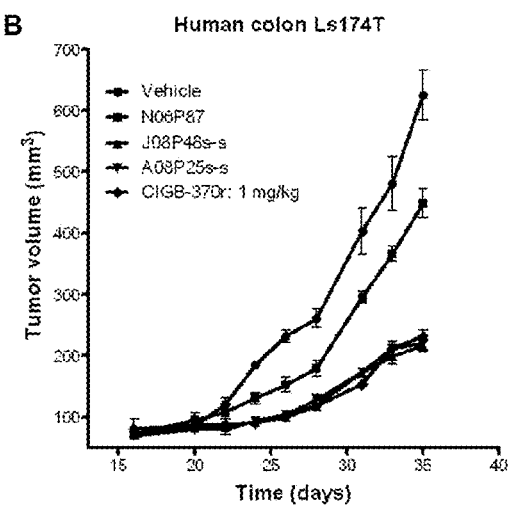
Figure 19:
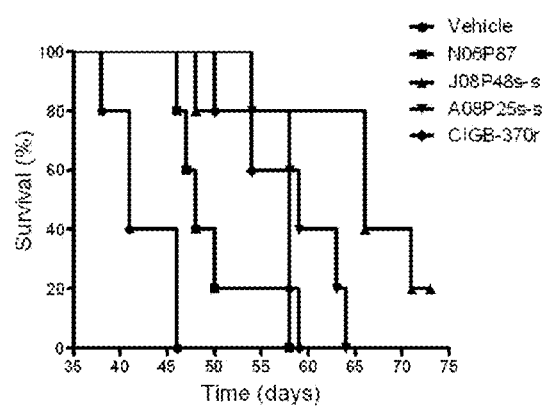

The effects of the linear segment Gly255-Ser274 (peptide N06P87) and two other model cyclic peptides of the present invention were compared to the effect of the CIGB370r polypeptide in the Ls174T human colon cancer model in athymic NIH mice, with the dose and schedule shown in FIG. 19. After 13 days, once the tumors were implanted and palpable, biomolecules began to be administered (FIG. 19 A). The peptides were administered in down-scaled doses: 2 administrations of 600 µM every 48 h, followed by 4 administrations of 330 µM each every 48 h, and 4 final 90 µM administrations every 72 h. The CIGB370r was administered weekly during 4 weeks.

In this case, and different from the linear peptide, cyclic peptides shown in FIG. 19 were able to significantly increase the survival of treated animals (Logrank test: p<0.05), compared to the group receiving the vehicle and to the linear N06P87 peptide. T/C values related to the mean tumor volume (FIG. 19B) were: 35%, 35%, 37%, and 72%, for the A08P25s-s, J08P48s-s, CIGB370r and N06P87 peptides, respectively. These results demonstrate that the cyclic peptides of the present invention, mimicking the tridimensional structure of the antitumor active site of p25, are useful for developing antineoplastic therapies. The peptides of the present invention show several pharmacokinetic and pharmacodynamic advantages compared to their native proteins.

Example 13

Wide Action Spectrum of the Cyclic Peptides of the Present Invention on Human Tumor Cell Lines of Diverse Histological Origin The peptides of the present invention were evaluated on various human tumor cell lines, of diverse histological origin, and using the sulforhodamine B method (Skehan P, Storeng R, Scudiero D, et al., (1990) "New colorimetric cytotoxicity assay for anticancer-drug screening". J. Natl. Cancer Inst. 82: 1107-1112).

Figure 18:
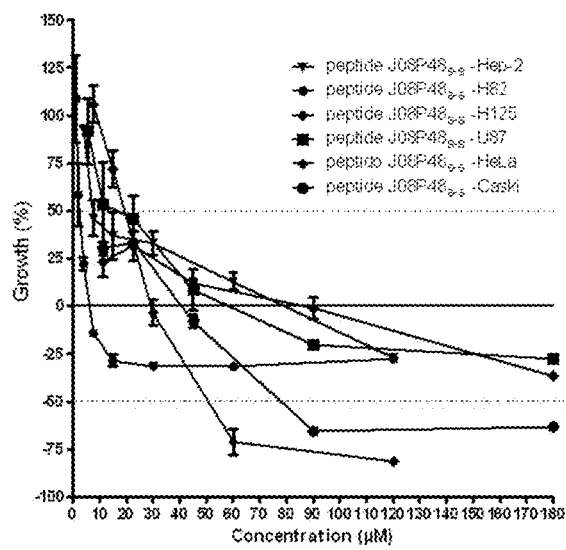
FIG. 18. Biological activity in vitro of the J08P48s-s on human tumor cell lines from different histological origins.

FIG. 18 shows, as example, a peptide of wide action spectrum on the cell lines evaluated, showing a dose-response effect. This evidences that these novel molecules are useful to treat malignant tumors for diverse histological origin, such as: larynx carcinoma (HEp-2), small cell lung cancer (H82), non-small cell lung cancer (H125), cervix uterine cancer (HeLa, Caski), and gliomas (U87), among others.

Example 14

Inhibition of Tubular Structure Formation in Matrigel

Figure 20:
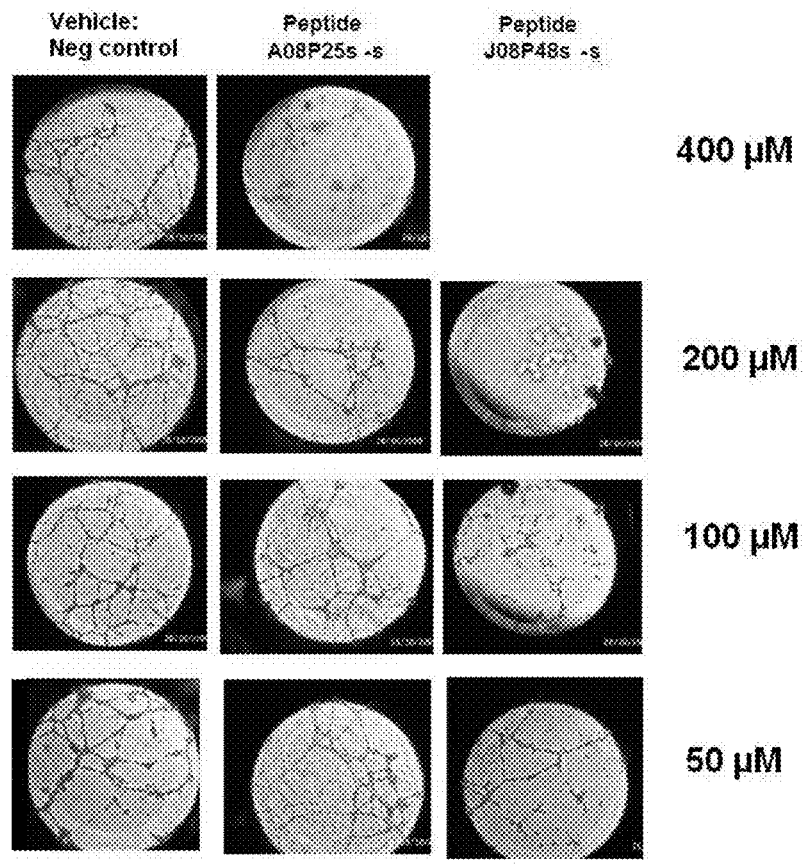
FIG. 20. Effect of two cyclic peptides of the present invention on the cellular differentiation of endothelial cells in matrigel. HMEC cells were cultivated under activation conditions (10 ng/mL EGF, 1 µg/mL hydrocortisone) in the presence of two cyclic peptides of the present invention or the excipient. The peptides were capable of inhibiting the formation of tubular structures by endothelial cells activated for proliferation, evidencing the antiangiogenic activity of the peptides, while the excipient allowed the formation of such tubular structures.

Currently, the international scientific community has well established that combination is the key for cancer therapy, especially by combining the direct action on tumor cells (inhibiting their proliferation or originating their death) together with the action on the tumor environment to inhibit angiogenesis. For that reason, the antiangiogenic activity of the peptides of the present invention was evaluated, by the method evaluating the formation of endothelial cell strands by human vasculature-derived endothelial cells (HMEC) on matrigel (Crum R, Szabo S, Folkman J. (1985). Science. 230:1375-8). FIG. 20 shows the capacity of cyclic peptides of the present invention to inhibit the formation of tubular structures, depending on the concentration used, and showing their antiangiogenic activity.

Example 15

Peptide Structures with Self Assembly Properties, Based on Cyclic Peptides Derived from *Serratia marcescens*

Figure 21:
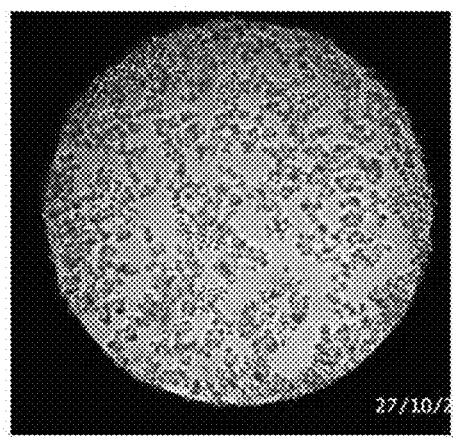
FIG. 21. Micrograph of the cyclic peptides of the present invention in conditions favoring their self-assembly.

The peptides of the present invention bear amphipathic character, provided by the segregation of hydrophobic and hydrophilic patches on the surface of the peptides. The hydrophobic patch is formed mainly by side chains of residues Tyr259, Phe269 and Leu270, which resemble their structure on the 3D structure of the p50 protein. The rest of the surface is formed, mainly, by polar or charged residues. This amphipathic character allows peptides to form nanometric and/or micrometric supramolecular aggregates, as shown in the FIG. 21 micrograph. The aggregation of peptides can be additionally mediated by the formation of intermolecular hydrogen bridges involving segments of the main chain and side chains. The extended structures of the N- and C-terminus secondary segments of the peptides of the present invention can favor a type of aggregation under certain formulation conditions, for novel applications in cancer therapy, such as: combined therapy and in the field of nanobiotecnology and controlled release systems (Monica C. Branco, Joel P. Schneider. Acta Biomaterialia 5 (2009) 817-831).

Example 16

Antitumoral and Antiangiogenic Cyclic Peptides Combined with Prodigiosin, Showing Synergic Cytotoxic Effect on Tumor Cells Prodigiosins isolated from *Serratia marcescens* CMIB4202 (Abrahantes-Pérez M C, Reyes-González J, Véliz Ríos G, et al., (2006) Cytotoxic proteins combined with prodigiosin obtained from *Serratia marcescens* have both broad and selective cytotoxic activity on tumor cells. J. Chemother. 18: 172-81) were combined with cyclic peptides of the present invention, by adequate formulations, or by means of covalent bonds, either by direct chemical synthesis or by chemical reactions between single molecules. Cyclic peptides such as A08P25s-s, A08P28s-s, J08P46s-s and J08P48s-s enhanced the cytotoxic activity of prodigiosin on the different human tumor cell lines (as A549, A375, PC-3, U87, etc.) evaluated by the SRB method (Skehan P, Storeng R, Scudiero D, et al., (1990) "New colorimetric cytotoxicity assay for anticancer-drug screening". J. Natl. Cancer Inst. 82: 1107-1112), showing GI50 values in the nm range, and decreasing the cytotoxic activity resulting from the action of prodigiosin on primary fibroblasts in at least one order of magnitude. This suggests that that the mechanisms of action of both molecules differ to each other and therefore, they can be combined with advantageous results in cancer therapeutics.

Example 17

Obtaining a Pharmaceutical Composition of Antitumoral and Antiangiogenic Cyclic Peptides Encapsulated with Polymers of the Family of the Polylactic-Co-Glycolic Acid (PLGA)

In order to modify the pharmacokinetics and biodistribution of the peptides of the present invention, according to the oncological therapeutic indication desired for each particular case, it was explored the encapsulation of these cyclic peptides together with polymers in PLGA microspheres. For this purpose, a solution was prepared containing the copolymer of lactic acid and plycolic acid 50:50 at 10% (w/v) by dissolving 1 g of the polymer in dichloromethane. One milliliter of the polymeric solution was mixed with 200 µL of an aqueous solution containing at least one of the peptides of the present invention, such as the A08P25s-s, A08P28s-s, J08P46s-s and J08P48s-s peptides at concentrations ranging 20-40 mg/mL. This mix was sonicated for 30 s by using a tip ultrasound. The resulting emulsion was poured on 40 mL of 1% polyvinyl alcohol and the second emulsion was obtained (w/o/w) by agitation of the two phases at 14 000 in an Ultraturrax T8 homogenizer. The double emulsion was poured on 140 mL of 0.1% polyvinyl alcohol 30 000-70 000 and was agitated in a homogenizer at 300 rpm for 1 h to evaporate the dichloromethane. Finally, microspheres were collected by filtration, washed five times with 50 mL of distilled water each, and freeze/dried in a lyophilizer. The dry microspheres were stored at 4° C. until application.

Microspheres containing cyclic peptides such as A08P25s-s, A08P28s-s, J08P46s-s, J08P48s-s with excipients were obtained as described, but adding Pluronic F-127 (10 mg) and NaCl (0.5 mg) in the inner aqueous phase. Both types of microspheres were administered subcutaneously near the tumors in athymic mice carrying implanted human melanoma A375 tumors. A single dose was administered when tumors reached volumes above 200 mm³, achieving results similar to those obtained after multiple administrations (thrice a week for 4 weeks), for T/C ratios lower than 10% for tumor volume and higher than 170% for survival.

Example 18

Obtaining Conventional Liposomes Loaded with Antitumoral and Antiangiogenic Cyclic Peptides Phosphatidyl choline, at a 10 mg/mL concentration, was dissolved in absolute ethanol in a 50 mL round-bottom flask. The lipid was dried by means of rotoevaporation at room temperature until a dry layer formed at the walls of the recipient. For the purpose of encapsulating in liposomes at least one of the cyclic peptides described in the present invention, such as A08P25s-s, A08P28s-s, J08P46s-s and J08P48s-s, the dry lipid layer was hydrated by homogenization with a buffered solution containing at least one of the previously mentioned peptides. To reduce the size of the liposomes, the preparation containing the liposomes loaded with the said peptides was subjected to successive extrusion steps through a polycarbonate membrane with pores of an average of 100 nm in diameter, until the liposomes were about 100 nm in size.

The free peptides were separated from the peptide-loaded liposomes by centrifuging the suspension at 100 000×g for 40 min at 4° C. The supernatant was collected into a clean vial and the precipitate re-suspended with a phosphate buffered saline solution at pH 7.2. After a second centrifugation step at the same conditions, the resulting supernatant was collected into a clean vial and mixed with the first centrifugation supernatant. The precipitate (liposomes loaded with the cyclic peptides of the present invention) was resuspended in a phosphate buffered saline solution at pH 7.2. This final preparation was stored at 4° C. until use. Liposomes loaded with at least one of the peptides of the present invention were administered as single dose to mice carrying the TC-1 tumor, reproducing the results obtained after multiple administrations of the unencapsulated peptides (see Example 12).

Example 19

Antitumoral and Antiangiogenic Cyclic Peptides with Capacity for Binding Metal Ions and Direct the Drug to a Specific Organ The amino acid composition of the peptides of the present invention provides the capacity to bind metal ions as radiometals and paramagnetic metals for using them as pharmaceuticals, without affecting their biological properties.

The peptide-metal ion complex can be generated by different physic-chemical procedures, at the sites indicated in previous examples. Among the radiometals we could find the isotopes of Tc, Re, Au, Ag, Pd, As, Cu, Hg, and Ru. The product of the reaction between the metal ion and the peptide is a complex between both molecules, which demonstrated to target specifically tumors and metastasis of diverse histological origin in animal models (C57BL/6 mice) carrying the TC-1 tumor. These complexes can be used for cancer diagnosis and therapeutics in a very specific manner, minimizing their uptake by physiologically normal tissues and organs.

For the case of complexes of peptides of the present invention with radioisotopes for cancer diagnosis and therapy, radioisotopes can be, for example: $^{99}$Tc and $^{131}$I. The metal-bound peptides, as explained in this invention, can be used for administration directly or conjugated to other carrier molecules.

In order to target the peptides of the present invention directly to the tumor for achieving their accumulation within it, compared to normal tissues and organs, a complex was synthesized formed by peptides, such as A08P25s-s, A08P28s-s, J08P46s-s and J08P48s-s, covalently linked to polyethylene glycol according to Example 8. They were further formulated with iron oxide nanoparticles, generating a magnetic nanoparticulated vector complex which major constituents were: the antitumoral cyclic peptides of the present invention, the polymer molecule and the iron oxide nanoparticle. The complex was administered intravenously (by the mouse tail vein) to C57BL/6 mice carrying the TC-1 subcutaneous tumor (located at the right flank of the animals) when the tumor volume was above 200 mm³. An external magnetic field was locally applied to the tumor region and the complex was transported through the blood stream and concentrated at the tumor (Lübbe A S, Bergemann C, Alexiou C. Targeting tumors with magnetic drugs. In: Pagé M, editor. Cancer drug discovery and development: tumor targeting in cancer therapy. Totowa N.J.: Humana Press Inc; 2003. pp. 379-88). Administration schedule and dose similar to that shown in Example 12 were used as control group, and the negative control group only received the vehicle devoid of antitumoral peptides. The antitumoral effect in the group treated with the nanoparticulated magnetic vector carrying the antitumor peptides demonstrated to decrease the tumor volume earlier than the positive controls (p<0.05) and survival was significantly higher than in the rest of the groups (p<0.05). These results demonstrated the potential of this technology to achieve the therapeutic effect described for the cyclic peptides of the present invention, based on the capacity to concentrate a higher amount of therapeutic molecules on the tumor.

Example 20

Synergic Effect of Combining the Antitumor Andantiangiogenic Cyclic Peptides with Conventional Cytostatics Synergy of the antineoplastic effect of peptides of the present invention (such as A08P25s-s, A08P28s-s, J08P46s-s, J08P48s-s) when separately combined with a group of conventional cytostatics was evaluated, under the following experimental conditions. A549 cells (non-small lung cancer cells) were cultivated in 96-well plates in the presence of one of the peptides previously mentioned at a concentration range of 200-12.5 μM. Simultaneously, at least one of the cytostatics selected for this study was added (Cisplatin, Paclitaxel, 5-Fluorouracil, Vincristine, Doxorubicin, Cyclophosphamide, Mitomycin C, Imatinib, Velcade, Iressa) at concentrations ranging 1-2000 nM, and the incubation was extended for 72. At that time, the cellular viability was revealed by the MTT method. Finally, the absorbance was measured at 570 nm for all the cases and the respective dose-response curves were plotted. Dose values reducing 50% of the cellular proliferation (IC50) for each cytostatic were lowered in one or two orders of magnitude when they were simultaneously combined with at least one of the peptides of the present invention. The results of these assays demonstrate an enhancement of the antineoplastic effect of the pharmaceutical combination comprising the cyclic peptides of the present invention together with the cytostatic compounds mentioned in this invention.

Example 21

Enhancement of the Antitumoral Effect of the Pharmaceutical Combination in an Animal Model of Cancer For this purpose, $5 \times 10^6$ A549 cells were inoculated by subcutaneous route at the dorsal region in 6-to-8 weeks-old nude mice (Balb/C mice). After 10 days, when tumors were detectable (about 30 mm$^3$), the pharmaceutical combination of the invention was administered. Components of the combination were administered by the intraperitoneal route, comprising at least one of the cyclic peptides of the present invention (such as: A08P25s-s, A08P28s-s, J08P46s-s and J08P48s-s), formulated in an adequate vehicle and under the same schedule and dose shown in Example 12. Cytostatics like Cisplatin, Cyclophosphamide and Mitomycin C were simultaneously provided by an intraperitoneal daily administration of 1 mg/kg of body weight, with the same treatment frequency. Cytostatics were dissolved in the same vehicle as the peptides. Finally, the tumor masses volumes were measured and plotted vs. time to evaluate the antineoplastic effect in vivo. Results indicated that the pharmaceutical combination of the invention produces an enhancement of the antitumor effect, promoting the complete regression of the tumor mass when both ingredients are administered simultaneously. A significant inhibition of tumor growth and also significant increase in animal survival were observed, compared to the placebo group. All these demonstrate that the synergic action between the components of the pharmaceutical combination of the invention is also effective in vivo, according to the results obtained in a relevant and predictive preclinical model of cancer.

INCORPORATION OF SEQUENCE LISTING

Incorporated herein by reference in its entirety is the Sequence Listing for the above-identified Application. The Sequence Listing is disclosed on a computer-readable text file titled "976-85 PCTUS Sequence.txt", created on Sep. 18, 2013. The sequence.txt file is 21.2. KB in size.

The invention claimed is:

1. A cyclic peptide having antineoplastic and antiangiogenic activities having an amino acid sequence selected from the group consisting of SEQ ID NOS: 1-76.

2. A cyclic peptide according to claim 1, characterized by having the N-terminus covalently linked to the acetyl group, the pyroglutamic amino acid, to a lipid or a polymer, and the bond could be established directly or through a spacer group.

3. A cyclic peptide according to claim 1, characterized by having the C-terminus in the amide form, or covalently linked to a lipid or a polymer, and the bond being established directly or through a spacer.

4. A method of treating cancer, undesired cellular proliferation-related disorders and undesired angiogenesis, wherein said method comprises administrating a pharmaceutical composition comprising an effective amount of at least one of cyclic peptides of claim 1 to an individual in need thereof.

5. The method of claim 4, characterized by the said pharmaceutical composition additionally comprising an agent selected from the group consisting of non-fluorescent group, a fluorescent semiconductor particle, a paramagnetic or superparamagnetic agent, and a radioisotope.

6. A pharmaceutical composition comprising at least one of the peptides from claim 1 and excipients or pharmaceutically suitable vehicles.

7. The pharmaceutical composition according to claim 6 wherein the peptides are in a controlled released system.

8. The pharmaceutical composition according to claim 7 wherein said controlled release system comprises liposomes.

9. The pharmaceutical composition according to claim 7 wherein said controlled release system comprises microspheres.

10. The pharmaceutical composition according to claim 7 wherein said controlled release system comprises self-assembling structures.

11. The pharmaceutical composition according to claim 6 wherein said composition additionally comprises an agent selected from the group consisting of a semiconductor particle, a paramagnetic or superparamagnetic agent, and a radioisotope.

12. A compound for diagnosing cancer comprising at least one of the peptides of claim 1 and an imaging agent, wherein said imaging agent is selected from the group consisting of a fluorescent group, a non-fluorescent group, a semiconductor fluorescent particle, a paramagnetic or superparamagnetic agent, and a radioisotope.

13. A pharmaceutical combination comprising at least one of the peptides of claim 1 together with at least one treatment agent selected from the group consisting of anticancer drugs and hormones.

14. The combination of claim 13 wherein said peptide is conjugated to the said treatment agent by covalent bonds.

15. The combination of claim 13 wherein said peptide is conjugated to said treatment agent by a coupling element.

16. The pharmaceutical combination of claim 15 wherein the coupling agent is selected from the group consisting of an amino acid residue, a hydrocarbyl and a substituted hydrocarbyl.

17. A pharmaceutical combination comprising at least one of the peptides from claim 1 and prodigiosins or their derivatives.

18. The cyclic peptide according to claim 2, wherein the lipid or polymer is polyethylene glycol.

19. The cyclic peptide according to claim 3, wherein the lipid or polymer is polyethylene glycol.

20. The cyclic peptide according to claim 2, wherein the spacer is the amino acid Gly.

21. The cyclic peptide according to claim 3, wherein the spacer is the amino acid Gly.

* * * * *